US007226735B2

(12) United States Patent
Jeffries et al.

(10) Patent No.: US 7,226,735 B2
(45) Date of Patent: Jun. 5, 2007

(54) XYLOSE-FERMENTING RECOMBINANT YEAST STRAINS

(75) Inventors: Thomas W. Jeffries, Madison, WI (US); Yong-Su Jin, Cambridge, MA (US)

(73) Assignees: Wisconsin Alumni Research Foundation, Madison, WI (US); The United States of America as represented by the Secretary of Agriculture, Washington, DC (US)

( * ) Notice: Subject to any disclaimer, the term of this patent is extended or adjusted under 35 U.S.C. 154(b) by 246 days.

(21) Appl. No.: 10/348,464

(22) Filed: Jan. 21, 2003

(65) Prior Publication Data
US 2004/0142456 A1    Jul. 22, 2004

(51) Int. Cl.
*C12Q 1/68* (2006.01)
*C12Q 1/54* (2006.01)
*G01N 33/53* (2006.01)
*C12P 1/00* (2006.01)
*C12N 1/00* (2006.01)
*C12N 15/63* (2006.01)

(52) U.S. Cl. .................... 435/6; 435/7.31; 435/14; 435/41; 435/254.1

(58) Field of Classification Search .............. 435/41, 435/161, 440, 471, 243, 254.1, 255.1, 255.2
See application file for complete search history.

(56) References Cited

U.S. PATENT DOCUMENTS 5,789,210 A * 8/1998 Ho et al. .................... 435/163
6,071,729 A   6/2000 Shi et al.
2003/0157675 A1* 8/2003 Cordero Otero et al. ... 435/161

OTHER PUBLICATIONS

Jin, YS et al. Appl. Environ. Microbiol. 68: 1232-1239, 2002.*
Taylor et al, Conflicting levels of selection in the accumulation of mitchondrial defects in *Saccharomyces cerevisiae*, PNAS 99:3690-3694, 2002.*
Cho et al, *Pichia stipitis* Genes for Alcohol Dehydrogenase with Fermentative and Respiratory Functions, Appl. and Envtl. Micro. 64:1350-1358, 1998.*
Barua, M. et al., "Partial purification and characterization of a phosphoprotein phosphatase from sperm plasma membrane," Reprod. Fertil. Dev. (1999) 11:379-386.
Bieche, I. et al., "Novel approach to quantitative polymerase chain reaction using real-time detection: application to the detection of gene amplification in breast cancer," Int. J. Cancer (1998) 78:661-666.
Boeke, J.D. et al., "Ty elements transpose through an RNA intermediate," Cell (1985) 40:491-500.
Chang, S.F. and Ho, N.W., "Cloning the yeast xylulokinase gene for the improvement of xylose fermentation," Scientific Note. App. Biochem. Biotechnol. (1988) 17:313-318.

Chiang, L.-C. et al., "D-xylose fermentation to ethanol by *S. cerevisiae*," Appl. Environ. Microbiol. (1981) 42:284-289.
Cho, K.M. et al., "Delta-integration of endo/exo-glucanase and beta-glucosidase genes into the yeast chromosomes for direct conversion of cellulose to ethanol," Enzyme Microb. Technol. (1999) 25:23-30.
Christianson, T.W. et al., "Multifunctional yeast high-copy-number shuttle vectors," Gene (1992) 110:119-122.
Christova, N. and Galabova, D., "Phosphorylase phosphatase activity in *Saccharomyces cerevisiae*," 257.Z Naturforsch (1998) [C] 53:951-956.
Crabtree, H.G., "Observations of the carbohydrate metabolism in tumors," Biochem. J. (1929) 23:536-545.
De Preter, K. et al., "Quantification of MYCN, DDX1 and NAG gene copy number in neuroblastoma using a real-time quantitative PCR assay," Mod. Pathol. (2002) 15:159-166.
Deng, X.X. and Ho, N.W., "Xylulokinase activity in various yeasts including *Saccharomyces cerevisiae* containing the cloned xylulokinase gene," Scientific Note. Appl. Biochem. Biotechnol. (1990) 24-25:193-199.
Eisen, M.B., et al., "Cluster analysis and display of genome-wide expression patterns," Proc. Natl. Acad. Sci. USA (1998) 94:14863-14868.
Eliasson, A. et al., "Anaerobic xylose fermentation by recombinant *Saccharomyces cerevisiae* carrying XYL1, XYL2, and XKS1 in mineral medium chemostat cultures," App. Environ. Microbiol. (2000) 66:3381-3386.
Epstein, C.B. et al., "Genome-wide responses to mitochondrial dysfunction," Mol. Biol. Cell (2001) 12:297-308.
Forsburg, S.L. and Guarente, L., "Identification and characterization of HAP4: a third component of the CCAAT-bound HAP2/HAP3 heteromer," Genes Dev. (1989) 3:1166-1178.
Hereford, J.B. and Rosbash, M., "Number and distribution of poly-adenylated RNA sequences in yeast," Cell (1977) 10:453-462.
Herrero, P. et al., "Transcriptional regulation of the *Saccharomyces cerevisiae* HXK1, HXK2 and GLK1 genes," Yeast (1995) 11:137-144.
Hinnebusch, A.G., "Translational regulation of yeast GCN4. A window on factors that control initiator-trna binding to the ribosome," J. Biol. Chem. (1997) 272:21661-21664.
Ho, N.W.Y. et al., "Genetically engineered *Saccharomyces* yeast capable of effective cofermentation of glucose and xylose," Appl. Environ. Microbiol. (1998) 64(5):1852-1859.

(Continued)

*Primary Examiner*—David Guzo
*Assistant Examiner*—Michele K. Joike
(74) *Attorney, Agent, or Firm*—Michael Best & Friedrich LLP

(57)   ABSTRACT

Disclosed are xylose-fermenting recombinant yeast strains comprising heterologous PsXYL1, Ps XYL2, and PsXYL3, as well as methods of fermenting xylose to obtain ethanol using the recombinant yeast strain.

12 Claims, 16 Drawing Sheets

OTHER PUBLICATIONS

Hodges, P.E., "The yeast protein database (YPD): a curated proteome database for *Saccharomyces cerevisiae*," Nucleic Acids Res. (1998) 26:68-72.

Hohmann, S. et al., "Evidence for trehalose-6-phosphate-dependent and -independent mechanisms in the control of sugar influx into yeast glycolysis," Mol. Microbiol. (1996) 20:981-991.

Holstege, F.C. et al., "Dissecting the regulatory circuitry of a eukaryotic genome," Cell (1998) 95:717-728.

Horiuchi, H. et al., "High level secretion of a *Rhizopus niveus* aspartic proteinase in *Saccharomyces cerevisiae*," Agric. Biol. Chem. (1990) 54(7):1771-1779.

Huh, W-K et al., J. Bact. (1999) 181(13):4098-4102.

Ingham, D.J. et al., "Quantitative real-time PCR assay for determining transgene copy number in transformed plants," Biotechniques (2001) 31:132-134, 136-140.

Jin, Y.S. and Jeffries, T.W., "Changing flux of xylose metabolites by altering expression of xylose reductase and xylitol dehydrogenase in recombinant *Saccharomyces cerevisiae*," Appl. Biochem. Biotechnol. (2002) 105-108:277-286.

Jin, Y.S. et al., "Conversion of xylose to ethanol by recombinant *Saccharomyces cerevisiae* containing genes for xylose reductase and xylitol dehydrogenase from *Pichia stipitis*," J. Microbiol. Biotechnol. (2000) 10:564-567.

Jin, Y.S. et al., "Optimal growth and ethanol production from xylose by recombinant *Saccharomyces cerevisiae* require moderate D-xylulokinase activity," Appl. Environ. Microbiol. (2003) 69:495-503.

Johansson, B. et al., "Xylulokinase overexpression in two strains of *Saccharomyces cerevisiae* also expressing xylose reductase and xylitol dehydrogenase and its effect on fermentation of xylose and lignocellulosic hydrolysate," App. Environ. Microbiol. (2001) 67:4249-4255.

Kingsman, A.J. and Kingsman, S.M., "Ty: A retroelement moving forward," Cell (1988) 53:333-335.

Kotter, P. and Ciriacy, M., "Xylose fermentation by *Saccharomyces cerevisiae*," Appl. Microbiol. Biotechnol. (1993) 38:776-783.

Kurtzman, C.P., "Molecular taxonomy of the yeasts," Yeast (1994) 10:1727-1740.

Lai, K. and Elsas, L.J., "Overexpression of human UDP-glucose pyrophosphorylase rescues galactose-1-phosphate uridyltransferase-deficient yeast," Biochem. Biophys. Res. Commun. (2000) 271:392-400.

Maleszka, R. and Schneider, H., "Involvement of oxygen and mitochondrial function in the metabolism of D-xylulose by *Saccharomyces cerevisiae*," Arch. Biochem. Biophy. (1984) 228:22-30.

Nissen et al. "Anaerobic and aerobic batch cultivations of *Saccharomyces cerevisiae* mutants impaired in glycerol synthesis," Yeast (2000) 16:463-474.

Olesen et al., "Yeast HAP2 and HAP3 activators both bind to the CYC1 upstream activation site, UAS2, in an interdependent manner," Cell (1987) 51:953-961.

Parekh, R.N. et al., "An integrating vector for tunable, high copy, stable integration into the dispersed Ty delta sites of *Saccharomyces cerevisiae*," Biotechnol. Prog. (1996) 12:16-21.

Reifenberger, E. et al., "Kinetic characterization of individual hexose transporters of *Saccharomyces cerevisiae* and their relation to the triggering mechanisms of glucose repression," Eur. J. Biochem. (1997) 245:324-333.

Richard, P. et al., "The role of xylulokinase in *Saccharomyces cerevisiae* xylulose catabolism," FEMX Microbiol. Lett. (2000) 190:39-43.

Rizzi, M. et al., "Purification and properties of the NAD+ xylitol dehydrogenase from the yeast *Pichia stipitis* .5," J. Ferment. Bioeng. (1989) 67:20-24.

Rodriguez-Pena, J.M. et al., "The YGR194c (XKS1) gene encodes the xylulokinase from the budding yeast *Saccharomyces cerevisiae*," FEMS Microbiol. Lett. (1998) 162:155-160.

Rose, M.D. et al., "Methods in yeast genetics A Laboratory Course Manual," Cold Spring Harbor, NY: Cold Spring Harbor Laboratory Press (1990).

Senac, T. and Hahn-Hagedahl, B., "Intermediary metabolite concentrations in xylulose- and glucose-fermenting *Saccharomyces cerevisiae* cells," Appl. Environm. Microbiol. (1990) 56:120-126.

Shamanna, D.K. and Sanderson, K.E., "Uptake and catabolism of D-xylose in *Salmonella typhimurium* LT2," J. Bacteriol. (1979) 139:64-70.

Sikorski, R.S. and Hieter, P., "A system of shuttle vectors and yeast host strains designed for efficient manipulation of DNA in *Saccharomyces cerevisiae*," Genetics (1989) 122:19-27.

Tantirungkij, M. et al., "Construction of xylose-assimilating *Saccharomyces cerevisiae*," J. Germent. Bioeng. (1993) 75:83-88.

Tantirungkij, M. et al., "Fed-batch fermentation of xylose by a fast-growing mutant of xylose-assimilating recombinant *Saccharomyces cerevisiae*," Appl. Microbiol. Biotechnol. (1994) 41:8-12.

Teusink, B., "The danger of metabolic pathways with turbo design," Trends Biochem. Sci. (1998) 23:162-169.

Thevelein, J.M. and Hohmann, S., "Trehalose synthase: guard to the gate of glycolysis in yeast?" Trends. Biochem. Sci. (1995) 20:3-10.

Toivari, M.H. et al., "Conversion of xylose to ethanol by recombinant *Saccharomyces cerevisiae*: importance of xylulokinase (XKS1) and oxygen availability," Metab. Eng. (2001) 3:236-249.

Tuleva, B. et al., "A specific alkaline phosphatase from *Saccharomyces cerevisiae* with protein phosphatase activity," FEMS Microbiol. Lett. (1998) 161:139-144.

Walfridsson, M. et al., "Expression of different levels of enzymes from the *Pichia stipitis* XYL1 and XYL2 genes in *Saccharomyces cerevisiae* and its effects on product formation during xylose utilisation," Appl. Microbiol. Biotechnol. (1997) 48:218-224.

Wang, P.P. and Schneider, H., "Growth of yeasts on D-xylulose," Can. J. Microbiol. (1980) 26:1165-1168.

Jin, Y-S. et al., "Genome-wide expression analysis of xylose metabolism in recombinant *Saccharomyces cerevisiae* expressing PsXYL1, PsXYL2, and PsXYL3," (Apr. 28, 2002) XP002376074 [Retrieved from the Internet http://www.ct.ornl.gov/symposium/24th/index_files/O2_04.htm, on Mar. 20, 2006].

* cited by examiner

| Strains | Gene | Copy / Promoter | Glucose (3 days) | Xylose (5 days) | Growth rate on xylose |
|---|---|---|---|---|---|
| FPL-YS314 | Control | S | | | 0.130 |
| FPL-YS424 | Control | S | | | 0.127 |
| FPL-YS2831 | Control | M / G | | | 0.135 |
| FPL-YS31N | PsXYL3 | S / N | | | 0.123 |
| FPL-YS32N | PsXYL3 | M / N | | | 0.109 |
| FPL-YS42 | ScXKS1 | M / G | | | 0.092 |
| FPL-YS32 | PsXYL3 | M / G | | | 0.063 |

XYLOSE-FERMENTING RECOMBINANT YEAST STRAINS

STATEMENT REGARDING FEDERALLY SPONSORED RESEARCH OR DEVELOPMENT

This invention was made with United States government support awarded by the following agencies:
DOE: DE-AC36-98G010337.
The United States has certain rights in this invention.

CROSS-REFERENCE TO RELATED APPLICATIONS

Not applicable.

BACKGROUND OF THE INVENTION

Within the United States, there is considerable interest in developing alternative energy sources to reduce dependence on foreign oil and nonrenewable energy. The use of ethanol as a fuel has become increasingly prevalent in recent years.

One way to meet the demand for ethanol production is to convert sugars found in biomass, i.e., materials such as agricultural wastes, corn hulls, corncobs, cellulosic materials, and the like to produce ethanol. In biomass conversion, microorganisms are used as biocatalysts to convert cellulosic materials to usable end products, such as ethanol. Efficient biomass conversion in large-scale industrial applications requires a microorganism that is able to tolerate high concentrations of sugar and ethanol, and which is able to ferment more than one sugar simultaneously.

Biomass commonly contains xylose at relatively high concentrations, i.e., as high as 25% of the total dry weight. The D-xylose content of hardwood species and herbaceous angiosperms is about 17% and 31% of the total dry weight, respectively. Because agricultural residues, pulping wastes, and fast-growing hardwood species have a high xylose content, the potential economic and ecologic benefits of converting xylose in these renewable materials are significant. In order for biomass conversion to be economically feasible, a practical, large-scale use must be found for xylose.

The pentoses D-xylose and L-arabinose are among the most difficult sugars in biomass to metabolize. Bacteria can ferment pentoses to ethanol and other co-products, and bacteria with improved ethanol production from pentose sugars have been genetically engineered. However, these bacteria are sensitive to low pH and high concentrations of ethanol, their use in fermentations is associated with co-product formation, and the level of ethanol produced remains too low to make using these bacteria in large-scale ethanol production economically feasible.

In general, industrial producers of ethanol strongly favor using yeast as biocatalysts, because yeast fermentations are relatively resistant to contamination, are relatively insensitive to low pH and ethanol, and are easier to handle in large-scale processing. Many different yeast species use xylose respiratively, but only a few species use xylose fermentatively. Fermentation of xylose to ethanol by wild type xylose-fermenting yeast species occurs slowly and results in low yields, relative to fermentation rates and ethanol yields that are obtained with conventional yeasts in glucose fermentations. In order to improve the cost effectiveness of xylose fermentation, it is necessary to increase the rate of fermentation and the ethanol yields obtained.

What is needed in the art are new yeast strains and methods for fermenting xylose to produce ethanol.

BRIEF SUMMARY OF THE INVENTION

In one aspect, the present invention provides a recombinant xylose-fermenting yeast strain comprising heterologous polynucleotides comprising a PsXYL1, a PsXYL2, and a PsXYL3. Suitably, the polynucleotide comprising PsXYL3, comprises the promoter natively associated with the PsXYL3 coding sequence. Suitably, the strain expresses xylulokinase at a moderate level. In one embodiment, the recombinant strain comprises the PsXYL3 sequence integrated into its genome. Suitably, the recombinant strain may be a respiration deficient mutant. Suitable recombinant strains having wild-type or reduced respiration have been deposited as NRRL Y-30602 and NRRL Y-30603, respectively.

In another aspect, the present invention provides a method of producing ethanol from the fermentation of xylose comprising contacting a recombinant strain according to the invention with xylose-containing material under suitable conditions to produce ethanol.

Yet another aspect of the invention provides a method of obtaining a recombinant yeast expressing xylulokinase at a moderate level comprising transforming a recombinant strain of yeast comprising PsXYL1 and PsXYL2 with an expression vector comprising PsXYL3 operably associated with a yeast insertion sequence, growing the transformants in xylose-containing medium, and selecting transformants that exhibit rapid growth on xylose. The present invention includes recombinant strains of yeast expressing xylulokinase at a moderate level obtained by transforming a recombinant strain of yeast comprising PsXYL1 and PsXYL2 with an expression vector comprising PsXYL3 operably associated with a yeast insertion sequence, growing the transformants in xylose-containing medium, and selecting for rapid growth on xylose-containing medium.

BRIEF DESCRIPTION OF THE SEVERAL VIEWS OF THE DRAWINGS

FIG. 1 shows the effect of xylulokinase activity on growth of serially diluted strains of *S. cerevisiae* on glucose or xylose.

DETAILED DESCRIPTION OF THE INVENTION

Figure 2:
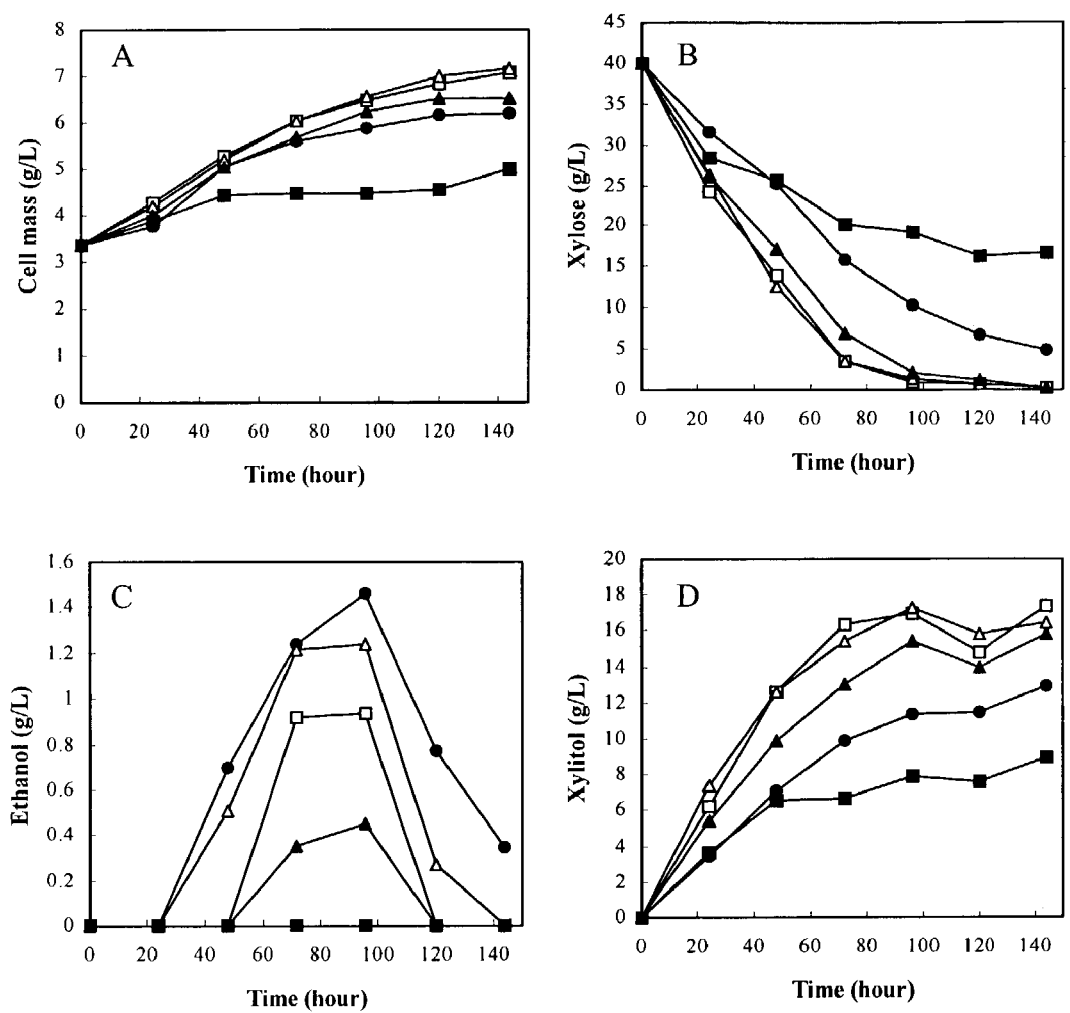
FIG. 2 shows differences between strains of *S. cerevisiae* with respect to cell growth (A), xylose consumption (B), ethanol production (C), and xylitol production (D) as a function of time.

Xylose utilization is critical to the economic feasibility of biomass fermentations. Although a few xylose-fermenting yeasts are found in nature (Kurtzman, 1994; Jeffries, 1983), *S. cerevisiae* is used ubiquitously for industrial ethanol production. Because *S. cerevisiae* cannot assimilate xylose, attempts to develop a strain of *S. cerevisiae* capable of using xylose have focused on adapting the xylose metabolic pathway from the xylose-utilizing yeasts, such as *Pichia stipitis* (Jin et al., 2000; Walfridsson et al., 1997; Kötter and Ciriacy, 1993; Tantirungkij et al., 1993). In *Pichia stipitis*, conversion of xylose to xylulose is catalyzed by two oxidoreductases. Xylose is reduced to xylitol by an $NAD[P]H^+$ linked xylose reductase (XR), and the xylitol is oxidized to xylulose by an $NAD^+$ linked xylitol dehydrogenase (XDH). Finally, D-xylulokinase (XK) phosphorylates D-xylulose to form D-xyluose-5-phosphate (X5P), which is metabolized further via the pentose phosphate pathway (PPP) and glycolysis (Jin et al., 2002). Because *S. cerevisiae* is able to ferment xylulose (Senac and Hahn-Hagedahl, 1990; Chiang et al., 1981; Wang and Schneider, 1980), early attempts to engineer xylose metabolism in *S. cerevisiae* involved expressing only XYL1 and XYL2 from *P. stipitis*, which encode XR and XDH, respectively (Jin et al., 2000; Walfridsson et al., 1997; Kötter and Ciriacy, 1993; Tantirungkij et al., 1993). Recombinant *S. cerevisiae* expressing AYL1 and XYL2 could grow on xylose, but ethanol production from xylose was not significant because a substantial portion of xylose was converted to xylitol (Jin et al., 2000; Tantirungkij et al., 1994; Kötter and Ciriacy, 1993).

Recombinant *S. cerevisiae* transformed with a single copy of XYL1 and multiple copies of XYL2 accumulate xylulose (Jin and Jeffries, 2002). This suggests that the native level of XK activity in *S. cerevisiae* limits xylose assimilation when XYL1 or XYL2 is overexpressed. Ho et al. (Ho et al., 1998) reported that overexpression of an endogenous *S. cerevisiae* XK gene (ScXKS1) with XYL1 and XYL2 increased ethanol production and decreased xylitol production from xylose. However, this observation remains controversial. Rodriguez-Pena et al. (Rodriguez-Pena et al., 1998) showed that overexpression of XKS1 in *S. cerevisiae* inhibits growth on pure D-xylulose. Other studies by Toivari et al. (Toivari et al., 2001) and Richard et al. (Richard et al., 2000) did not show an inhibitory effect from XK overexpression, but Johansson et al. (Johansson et al., 2001) found that overexpression of ScXKS1 reduced xylose consumption by 50 to 80% in *S. cerevisiae* transformants, even though it increased the yield of ethanol from xylose. Johansson et al. (Johansson et al., 2001) cautioned against the unmodulated overexpression of ScXKS1.

As used herein, XYL1, XYL2, and XYL3 refer polynucleotides comprising a sequence corresponding to the sequences from *P. stipitis* encoding XD, XR, or XK, respectively.

As described in the Examples below, a recombinant strain of *S. cerevisiae* capable of fermenting xylose to produce ethanol at relatively high rates was developed. In addition to recombinant *S. cerevisiae*, recombinant strains of economically important, ethanol producing yeast species include, but are not limited to, *Saccharomyces carlsbergensis* (*Saccharomyces pastorianus*), *Saccharomyces uvarum*, *Saccharomyces bayanus* and various hybrids of these and other yeast species used in brewing or winemaking, the thermotolerant yeast, *Kluyveromyces marxianus*, for use in high temperature simultaneous saccharification and fermentation of pre-treated lignocellulosic residues, and *Kluyveromyces lactis* for the fermentation of lactose in cheese whey.

The recombinant strain of *S. cerevisiae* developed, as described below, expresses XYL1 and XYL2 from *P. stipitis* under the control of the GAPHD (TDH1) promoter, a strong constitutive *S. cerevisiae* promoter, and was engineered to contain multiple copies of XYL3 with its native *P. stipitis* promoter integrated into the *S. cerevisiae* genome using a tunable expression vector that allows various expression levels by achieving different integrated copy numbers. Transformants thus obtained were screened for rapid growth on xylose, and transformants capable of growing rapidly on xylose were selected. Rapid growth on xylose was correlated with moderate levels of xylulokinase activity and relatively high levels of ethanol production. Xylulokinase expression may be affected by copy number and promoter strength. In general, recombinant strains having moderate expression of xylulokinase have neither single copy nor high copy numbers with respect to XYL3, and the expression of XYL3 is not under the control of a strong, constitutive promoter (Jin et al., 2003).

A recombinant xylose fermenting yeast strain exhibiting moderate expression of the xylulokinase is characterized by its capacity for rapid growth on xylose. As shown in the Examples, in contrast to a recombinant yeast strain exhibiting moderate expression of the xylulokinase, strains having low expression of xylulokinase grew relatively slowly, whereas overexpression of xylulokinase was toxic to yeast. Rapid growth on xylose is evaluated by comparing the cell growth of the transformant comprising XYL3 to that of the parent strain from which the transformant is derived, and may be expressed as relative cell growth, as described in the Examples. In the present invention, transformants having rapid cell growth had a relative cell growth of about 4.

One suitable recombinant *S. cerevisiae* strain comprising XYL1, XYL2, and multiple copies of XYL3 with its native *P. stipitis* promoter integrated into its genome, and exhibiting rapid growth on xylose and good ethanol production was selected and designated FPL-YSX3. The strain was deposited with the Agricultural Research Service Culture Collection in Peoria, Ill. on Jun. 5, 2002 under the Budapest Treaty and was assigned accession number NRRL Y-30602. A recombinant *S. cerevisiae* having the identifying characteristics of FPL-YSX3 comprises PSXYL1 and PsXYL2 under the control of a constitutive promoter, comprises PsXYL3 integrated into its genome, exhibits moderate expression of xylulokinase, and is able to ferment xylose to produce ethanol.

As described in the Examples, a recombinant *S. cerevisiae* strain expressing XYL1 and XYL2 was used to obtain FPL-YSX3 by means of a vector containing a δ sequence capable of integrating into a Ty transposon element. The XYL3 sequence was introduced into the vector, such that the sequence was operably associated with δ sequence. By 'operably associated' it is meant that the XYL3 and δ sequences are linked such that an insertion event involving the δ sequence results in insertion of the XYL3 sequence into a Ty transposon element in the yeast genome. It is specifically envisioned that, in addition to *S. cerevisiae*, other yeast species fermenting xylose and expressing moderate levels of xylulokinase may be obtained using the teachings of the present invention. As one of skill in the art will appreciate, the vector chosen to introduce the XYL3 into the yeast genome must be chosen with regard to the genetics of the particular species involved.

Strain FPL-YSX3 was used to obtain a respiration deficient mutant, designated FPL-YSX3P, which was deposited with the Agricultural Research Service Culture Collection in Peoria, Ill. on Jun. 21, 2002 under the Budapest Treaty and was assigned accession number NRRL Y-30603. As described below in the Examples, FPL-YSX3P was obtained by exposing a culture of FPL-YSX3 with the intercalating dye, ethidium bromide to obtain petite mutants lacking mitochondria. It is envisioned that respiration deficient mutants according to the present invention may be obtained by any suitable method, including using other DNA intercalating dyes in place of ethidium bromide. Shi et al. (U.S. Pat. No. 6,071,729) describes a respiration deficient mutant of *P. stipitis* obtained by disrupting the cytochrome c gene using a disruption cassette, and similar methods could be used to generate respiration deficient mutants according to the present invention. Another means by which respiration deficient mutants may be obtained would include irradiating yeast cells with ultra violet light. Because respiration deficient yeast mutants form petite colonies, mutants maybe be distinguished from wild type cells on the basis of colony size, and the respiration deficient status could be confirmed by measuring respiratory activity, by evaluating growth on xylose, or comparing ethanol production. A recombinant *S. cerevisiae* having the identifying characteristics of FPL-YSX3P comprises PsXYL1 and PsXYL2 under the control of a constitutive promoter, comprises PsXYL3 integrated into its genome, exhibits moderate expression of xylulokinase, is unable to grow on xylose, and exhibits increased fermentation of xylose to ethanol and reduced respiratory activity relative to FPL-YSX3.

In the Examples below, FPL-YSX3 was identified as a recombinant xylose-fermenting yeast strain exhibiting moderate expression of xylulokinase. Quantitation of the PsXYL3 sequence showed that FPL-YSX3 contains approximately three to four copies of PsXYL3. However, it is reasonably expected that suitable recombinant xylose-fermenting yeast strains according to the present invention having fewer or more copies of the PsXYL3 sequence will also exhibit moderate expression of xylulokinase. It is reasonably expected that strains comprising the PsXYL3 sequence integrated into the genome at a copy number ranging from one to 50 will exhibit moderate xylulokinase expression, i.e., rapid growth on xylose relative to the parent strain from which the recombinant strain is derived. The most effective copy number will depend on the promoter strength, its regulatory characteristics, and the yeast genetic background.

The sequence of XYL3 is deposited in GenBank under accession number AF127802, and the amino acid sequence of xylulokinase is deposited in GenBank under accession number AAF72328. It is understood that the XYL3 sequence used to obtain a recombinant strain according to the present invention may have minor variations, substitutions, additions or deletions relative to the XYL3 sequence identified by accession number AF127802, and it is well understood among those of ordinary skill in the art that certain changes in nucleic acid sequence make little or no difference to the overall function of the protein or peptide encoded by the sequence. Due to the degeneracy of the genetic code, particularly in the third position of codons, changes in the nucleic acid sequence may not result in a different amino acid being specified by that codon. Changes that result in an amino acid substitution to AAF72328 may have little or no effect on the three dimensional structure or function of the encoded protein or peptide. In addition, changes that result in insertions or deletions of amino acids may also be acceptable.

It is expected that recombinant yeast strains of the present invention may be further manipulated to achieve other desirable characteristics, or even higher specific ethanol yields. For example, selection of recombinant yeast strains by passaging the mutant yeast strains of the present invention on medium containing hydrolysate may result in improved yeast with enhanced fermentation rates. Suitably, the recombinant yeast strain is able to grow under conditions similar to those found in industrial sources of xylose. In the practice of the method of the present invention, the xylose-containing material can be inoculated with a suitable recombinant *Saccharomyces cerevisiae* without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors, which inhibit or prevent the growth of most organisms. Passaging of the yeast selects for yeast that are better able to grow in the presence of sulfite or phenolic inhibitors. Likewise, passaging the recombinant yeast under conditions that would select for faster fermentation could reasonably be expected to obtain further improvements. Such conditions would include cultivation on xylose under oxygen limitation or anaerobiosis in the presence or absence of glucose. Because overexpression of XYL3 or XKS1 results in growth inhibition when cultivated on xylose, selection for mutants that overcome such inhibition might reasonably be expected to result better growth and fermentation rates on xylose By "xylose-containing material," it is meant any medium comprising xylose, whether liquid or solid. Suitable xylose-containing materials include, but are not limited to, hydrolysates of polysaccharide or lignocellulosic biomass such as corn hulls, wood, paper, agricultural by-products, and the like.

Without being limited as to theory, we hypothesize that the inhibition of cell growth and ethanol production observed when cells express high levels of XK can be explained by substrate accelerated cell death. Thevelein et al. reported that growth of a *S. cerevisiae* tps1 mutant was markedly inhibited on glucose but not on other carbon sources (Thevelein and Hohmann, 1995). TPS1 encodes for trehalose-6-phosphate (Tre6P) synthase. A tps1 disruptant cannot synthesize Tre6P, a potent inhibitor of hexokinase (Hohmann et al., 1996). As a result, hexokinase in a tps1 background phosphorylates glucose without control of Tre6P, which causes an excess flux of glucose into glycolysis. Uncontrolled hexokinase activity in the tps1 mutant may deplete ATP and accumulate glucose-6-phosphate (G6P). Cells are inhibited by accumulation of G6P, depletion of ATP or by an imbalance between upstream and downstream enzymatic activities in the pathway. Teusink et al. call this paradoxical phenotype, in which enhanced utilization of substrate causes growth inhibition, "substrate accelerated cell death", and they have pointed out the danger of "turbo design" in metabolic engineering (Teusink et al., 1998). Catabolic pathways are similar to turbo engines in that energy input is required before energy output can be realized. However, the supply must be matched to demand through a feedback loop in order to operate efficiently. Turbo design involving strong overexpression can increase flux through a metabolic step, but this approach can be also deleterious if it breaks the balance between the reactions coupled to ATP synthesis and utilization. Without a regulatory feedback loop, overexpression of XK could be inhibitory. One approach to avoid this problem would be to attach an appropriately regulated promoter to XYL3.

Figure 7:
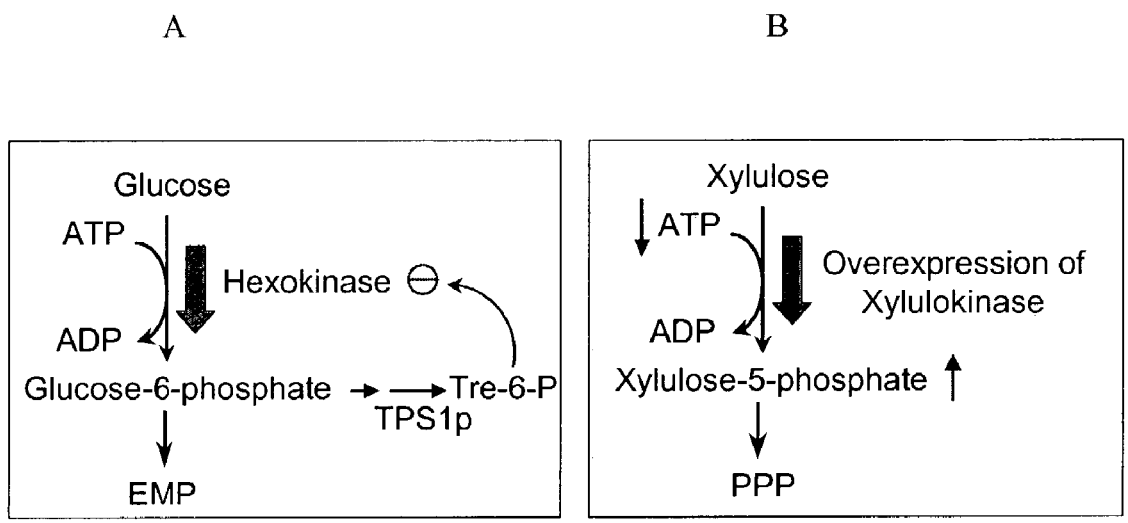
FIG. 7 shows a proposed model to explain substrate accelerated cell death in TPS1 disruptant (A) and *S. cerevisiae* overexpressing xylulokinase (B).
Figure 8:
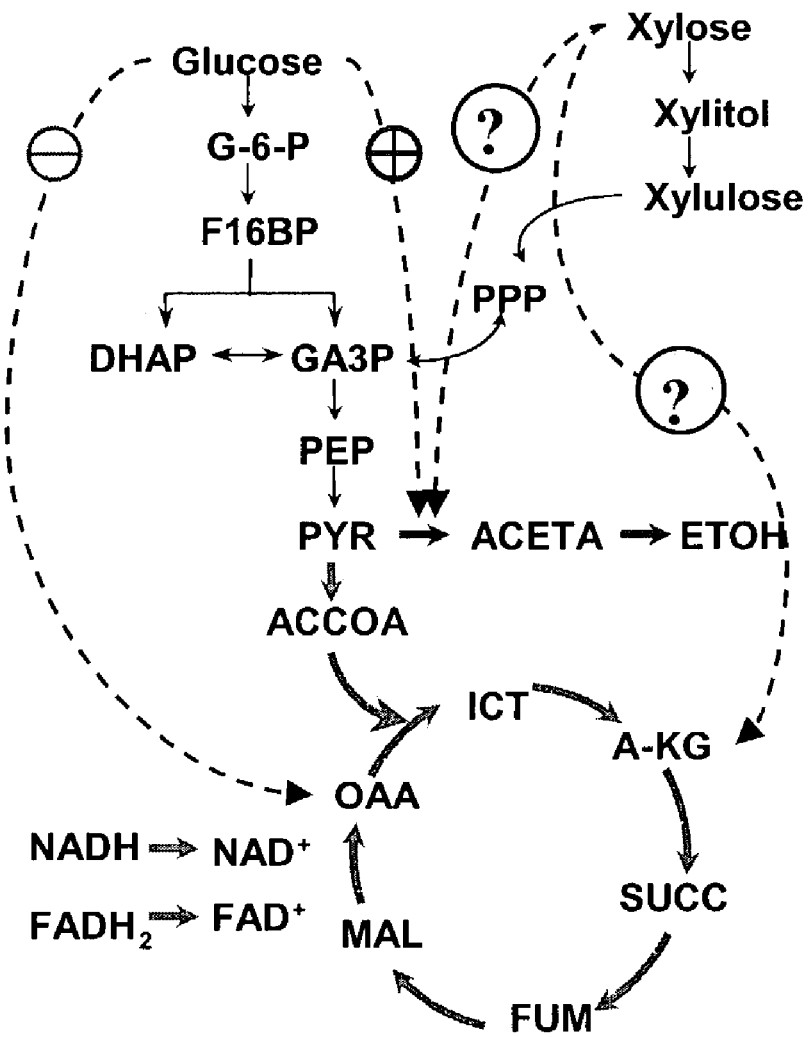
FIG. 8 shows a proposed hypothesis of glucose repression in *S. cerevisiae*.

Overexpression of XK in *S. cerevisiae* could be inhibitory for several reasons (FIG. 7). First, *S. cerevisiae* might not possess a guard system that prevents excessive ATP consumption in the presence of XK because this yeast has not evolved to utilize xylose. Rapid ATP depletion would then inhibit the cells because ATP is necessary for other cellular activities. Second, the PPP capacity in *S. cerevisiae* might be not sufficient to maintain metabolic flux at steady state for ATP synthesis when XK is overexpressed. Excess XK activity could then result in accumulation of X5P and depletion of ATP. Third, it is possible that X5P itself is toxic to the cell. The toxicity resulting from excess accumulation of sugar phosphate was previously reported for galactose metabolism (Lai and Elsas, 2000). Regardless of the exact mechanism, previous research by Toivari et al. supports this hypothesis because levels of X-5-P were significantly higher and levels of ATP were lower in an XK overexpressing strain as compared to parental strains (Toivari et al., 2001).

The inhibitory effect of higher XK activity that was observed during growth on agar plates correlated closely with the growth rate under fully aerobic conditions in liquid medium (FIG. 1). However, in the fermentative trials with low aeration, where growth rates were about one-tenth of those observed under the fully aerobic condition, only FPL-YS32, which has the highest XK activity, showed significant growth inhibition (FIG. 2A). This suggests that ATP demand in the cell and xylulose levels are responsible for the inhibitory effect observed with xylulose overexpression.

Under oxygen-limited conditions, the ATP demand would be greatly reduced relative to that under fully aerobic conditions, because cell growth is slower, and the inhibitory effect of xylulokinase overexpression would not be reduced. Alternatively, it is possible that the initial oxidoreducatase step for conversion of xylose into xylulose is limited by oxygen availability. Hence, the supply of xylulose to deplete ATP would be limited under fermentative conditions. Comparing XK activities among other studies may help resolve some of the apparent conflicts, although a direct comparison of XK activities may be imperfect due to differences between strains and assay methods. Rodriguez-Pena et al. (Rodriguez-Pena et al, 1998) first noted the toxicity of XK overexpression with cells grown on D-xylulose. Although XK activity was not reported, these researchers used a multicopy vector with a strong promoter. Johansson et al. (Johansson et al., 2001) reported XK activities of 28 U/mg and 36 U/mg in H158-pXks and CEN.PK-pXks from cells grown in defined media on a glucose/xylose sugar mixture. XK activities reported by these researchers should be compared to our XK activities in the cells grown on glucose because Johansson et al. prepared cell extracts from early batch cultures in which glucose was probably still present. Johansson et al. found XK overexpression to be deleterious, as characterized by the severe inhibition of xylose consumption. In those studies approximately 7 g/L of xylose was consumed within 125 hours whereas the parental strain consumed 40 g/L of xylose within the same period. These results suggest that overexpression of XK in *S. cerevisiae* is inhibitory when xylose is used as a carbon source. In contrast, Toivari et al. (Toivari et al., 2001), and Ho et al. (Ho et al., 1998) reported much lower XK activities (7 nkat/mg, i.e., 0.42 U/mg and 0.1 U/mg, respectively) in their recombinant *S. cerevisiae* than in FPL-YS32, H158-pXks (Johansson et al., 2001) and CEN.PK-pXks (Johansson et al., 2001). However, these values are still higher than the reported native XK activity. Both groups of researchers observed that overexpression of XKS1 significantly enhances xylose fermentation rather than causing toxic effects as was observed with XKS1 in FPL-YS32, H158-pXks (Johansson et al., 2001) and CEN.PK-pXks (Johansson et al., 2001).

These results suggest that the effects of heterologous XK expression on cell physiology can vary with the expression level, and that XK expression should be moderate. If heterologous XK expression is too high or too low, cells do not grow well on xylose; however, if XK expression is moderate, xylose metabolism is significantly enhanced. The appropriate level of XK might vary by intrinsic strain specific properties, such as XR and XDH activity, pentose phosphate pathway capacity, and respiration capacity, because it is related to cellular levels of X5P and ATP. Moreover, the optimum XK level can also be affected by extrinsic factors such as aeration, which mainly controls generation of ATP. Therefore, it is difficult to define optimal XK levels by forward engineering.

Figure 4:
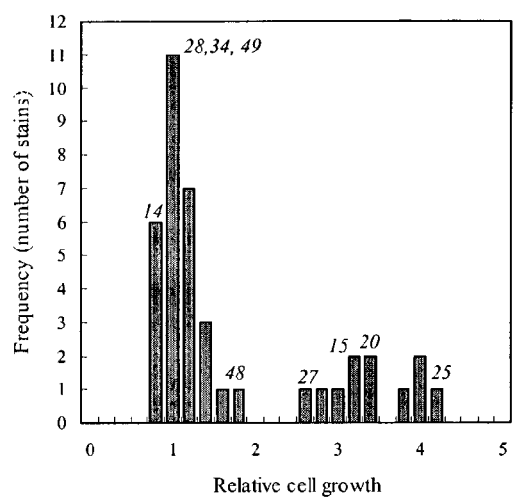
FIG. 4 shows to frequency of XYL3 transformants exhibiting different levels of relative cell growth (A) and cell mass, xylitol production, and ethanol production (B) for the strains.
Figure 4:
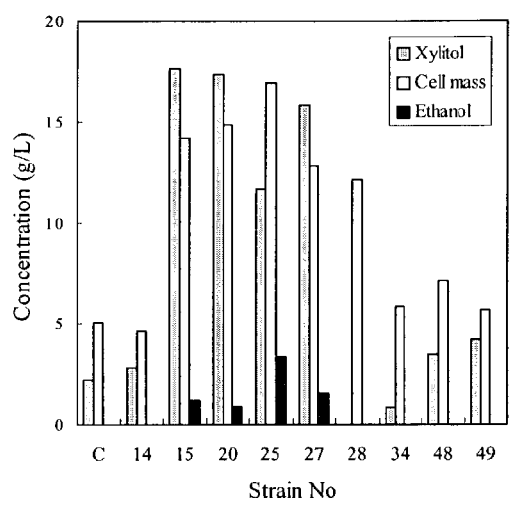

We used an empirical approach to select a strain that grew best on xylose after transforming the recipient host with a tunable expression vector. The vector is a plasmid that contains XYL3 and a δ sequence for homologous recombination into the chromosome at multiple δ sites. δ sequences are long terminal repeats (LTR) of Ty elements that can be used as targets for integration. We used G418 to select for transformants. The level of expression is essentially a linear function of the number of insertion sites. More than 100 copies of δ sequences exist in the yeast chromosome, so many contextual expression sites are possible. Resistance to G418 increases with copy number. Parekh, et al. (Parekh et al., 1996) found that the integrated copy number of the Ty integration vector ranges from 1 to 30 after a single transformation, that the level of amplification is stable over 50 generations in the absence of antibiotics, and that the chromosomal context around the integration site affects the expression of integrated gene. These two features (copy number and context of integration site) for tuning gene expression were employed to evaluate expression of XYL3. As expected, each transformant showed a different growth characteristic on xylose (FIG. 4A). Perhaps XK activity in the transformant could not reach high levels because the native *P. stipitis* promoter was used to drive XYL3 expression (Jin et al., 2002). Our activity and copy number results indicate that this promoter does not induce high transcript levels or enzymatic activity in *S. cerevisiae*.

Our results show the toxic effects of overexpression of XK genes (XKS1 and XYL3) during xylose fermentation by recombinant *S. cerevisiae*. These results suggest that levels of introduced enzyme activity should be designed in concert with the capacity of the surrounding metabolic network. Because numerous intrinsic and extrinsic factors affect the flow of metabolites in cells, we think that reverse engineering of metabolism, as shown in our study, would be a practical approach for developing strains with improved metabolic pathways.

The mRNA levels of recombinant *S. cerevisiae* harboring genes encoding enzymes required for the complete xylose metabolic pathway from *P. stipitis* under four different culture conditions (two carbon sources, two aeration conditions) were profiled. The results confirmed many known changes in gene expression patterns reported previously in response to environmental perturbations. For instance, the Crabtree effect was confirmed at the level of transcription, which is characterized by a tight repression of TCA cycle enzymes (ACO1, IDH2, KGD1, SDH1, and MDH1) and respiratory enzymes (QCR2 and COX5A) by glucose even under aerobic conditions. The known regulation of gene expression by oxygen was also verified. The mRNA level of Hap4p, which constitutes a critical component of the transcriptional activator complex Hap2/3/4, increased three-fold under aerobic conditions even with glucose as a carbon source.

In addition, unexpected changes in mRNA levels were identified. For instance, the mRNA levels of HXK1, FBP1, and PCK1 increased significantly when cells were grown on xylose, regardless of aeration conditions. Expression levels of HXK1, FBP1, and PCK1 are known to increase when cells are grown on nonfermentable carbon sources. Moreover, expression of TCA cycle enzymes and respiratory enzymes were not repressed by xylose in the same manner as glucose. Based on these results, we conclude that xylose is recognized as a non-fermentable carbon source by recombinant *S. cerevieiae*. This result supports the "repression hypothesis", i.e., xylose is poorly metabolized into ethanol because, in contrast to glucose, xylose does not repress respiration. However, mRNA levels of fermentative enzymes (ADH1 and PDC1) did not largely change in response to the change of carbon source, which suggests that the "induction hypothesis", i.e., that fermentative enzymes (PDC1 and ADH1) are not induced by xylose, is not valid. Another notable feature in genome-wide expression pattern is that expression of many oxidoreductases that use NADH or NADPH as cofactors was found to increase when cells are grown on xylose. The mRNA levels of GDH2, which encodes glutamate dehydrogenase, and LYS12, which encodes homoisocitrate dehydrogenase, increased significantly when cells are grown on xylose. These may function to alleviate redox imbalance. Changing intracellular redox balance by overexpressing GDH2 was demonstrated previously (Nissen, et al. 2000). Nissen et al. showed that product formation pattern could be changed from glycerol to ethanol under anaerobic conditions by oxidizing surplus NADH by overexpressing GDH2 in a gdh1 mutant.

To determine the reproducibility of our cultivation and analytical techniques, the base reference condition (high aeration on glucose) was chosen. A comparison of the variation of expression data between replicate experiments showed that only relatively few of the 5700 genes exhibited a change in expression of greater than two-fold between independent experiments. However, the greatest variations in expression were observed with genes expressed at fewer than 2 copies of mRNA per cell. Thus, if we filter out genes whose expression levels are low, we could reduce variation, although the resolution of our experiment would decrease. Therefore, two criteria were selected to filter out the genes whose expression is not changed much. First, we identified genes for which expression levels changed less than two-fold (Experiment/Base or Base/Experiment >2, which is equivalent to a two fold increase or decrease), and then we filtered out the genes whose absolute expression levels does not change much (Experiment-Base or Base-Experiment>100 in hybridization signal, which is equivalent to increase or decrease of mRNA of greater than 2 copies/cell). With those criteria, 99.8% of the remaining genes were within a two-fold difference between replicates. Additional trials and environmental controls would be necessary to derive more detailed analysis of the data.

The respiration deficient mutant, FPL-YSX3P ($\rho^\circ$ strain) did not grow on xylose, even though the FPL-YSX3P ferments xylose. This observation is consistent with the previous reports. Maleszka et al. found that *S. cerevisiae* required oxygen for growth on D-xylulose (Maleszka and Schneider, 1984), and petite mutants of *S. cerevisiae* did not grow on D-xylulose. Likewise, *S. cerevisiae* metabolically engineered with XYL1, XYL2 and XKS1 for the anaerobic production of ethanol from D-xylose did not grow on D-xylose under anaerobic conditions (Eliasson et al., 2000). These results suggest that mitochondria are involved in D-xylulose metabolism in *S. cerevisiae* (Wang and Schneider, 1980).

An interesting feature of the respiration deficient mutant FPL-YSX3P is that it showed improved fermentation capacity relative to its parental strain (FPL-YSX3) even though FPL-YSX3P could not grow on xylose. Surprisingly, FPL-YSX3P mutant produced less xylitol than the FPL-YSX3. Recently, Epstein et al. observed that respiratory deficiency induced expression of a series of genes associated with anaplerotic pathways that would mitigate the loss of a complete TCA cycle. This metabolic reprogramming would help to resolve the redox imbalance caused by cofactor differences between XR and XDH, which results in xylitol production.

EXAMPLES

Methods and Materials

Strains and Plasmids.

Microbial strains and plasmids used in this study are listed in Table 1. *Saccharomyces cerevisiae* L2612 (MATα leu2-3 leu2-112 ura3-52 trpl-298 can1 cyn1 gal+) and plasmid, pY2XK were provided by Prof. Jin-Ho Seo, of Seoul National University. The neo$^r$ based Ty-δ tunable expression vector, pITy4 was provided by Prof. Wirttrup, of MIT (Parekh et al., 1996). *Escherichia coli* DH5α (F$^-$ recA1 endA1 hsdR17 [$r_K^- m_K^+$] supE44 thi-1 gyrA relA1) (Gibco BRL, Gaithersburg, Md.) was routinely used for gene cloning and manipulation.

Media and Culture Conditions.

Yeast and bacterial strains were stored in 15% glycerol at −70° C. *E. coli* was grown in Luria-Bertani (LB) medium. When required, ampicillin (50 μg/ml) was added to the medium. Yeast strains were routinely cultivated at 30° C. in YP medium (10 g/L yeast extract, 20 g/L Bacto Peptone)

with 20 g/L glucose (YPD), 20 g/L xylose (YPX-2%) or 40 g/L xylose (YPX-4%). YPD or YPX plus 20 g/L of agar were used for plates. To select for yeast transformants using the URA3, TRP1 or LEU2 selectable markers, Yeast Synthetic Complete (YSC) medium containing 6.7 g/L Yeast Nitrogen Base (YNB) without amino acids plus 20 g/L glucose, 20 g/L agar and a mixture of appropriate nucleotides and amino acids was used. To select for transformants using the $neo^r$ marker, we used YPD agar supplemented with 200 μg/mL G418 (Geneticin, Sigma). Yeast cells were cultivated at 30° C. in 50 ml of medium in a 125 ml Erlenmeyer flask. To screen for XYL3 transformants, 40 putative transformants were inoculated into separate 5-ml aliquots of YPX-4% medium in 15 ml sterile culture tubes and incubated for 72 hours at 30° C. with shaking at 200 rpm. Cell growth and product formation were measured to identify ten strains for further screening. Selected strains were retested by culturing cells in 50 mL YPX-4% medium in 125 ml Erlenmeyer flasks shaken at 200 rpm.

TABLE 1

Strains and plasmids used in this study

| Strains or plasmids | Description | Source or reference |
|---|---|---|
| Strains | | |
| S. cerevisiae L2612 | MATα, trp1-112, leu2-1, ura3-52 | (Cho et al., 1999) |
| S. cerevisiae FPL-YS10 | MATα, trp1-112, leu2::LEU2-TDH1$_P$-XYL1-TDH1$_T$ | (Jin and Jeffries, 2002) |
| S. cerevisiae FPL-YS1020 | MATα, trp1-112, LEU2::GAPDH$_P$-XYL1-GAPDH$_T$, URA3::GAPDH$_P$-XYL2-GAPDH$_T$ | (Jin and Jeffries, 2002) |
| S. cerevisiae FPL-YSX3 | MATα, trp1-112, leu2::LEU2-PsXYL1, ura3::URA3-PsXYL2, Ty3::NEO-PsXYL3 | This study |
| S. cerevisiae FPL-YS314 | S. cerevisiae FPL-YS1020 (pRS314) | This study |
| S. cerevisiae FPL-YS424 | S. cerevisiae FPL-YS1020 (pRS314) | This study |
| S. cerevisiae FPL-YS2831 | S. cerevisiae FPL-YS1020 (pYPR2831) | This study |
| S. cerevisiae FPL-YS31N | S. cerevisiae FPL-YS1020 (pYS31N) | This study |
| S. cerevisiae FPL-YS32N | S. cerevisiae FPL-YS1020 (pYS32N) | This study |
| S. cerevisiae FPL-YS31 | S. cerevisiae FPL-YS1020 (pYS31) | This study |
| S. cerevisiae FPL-YS32 | S. cerevisiae FPL-YS1020 (pYS32) | This study |
| S. cerevisiae FPL-YS41 | S. cerevisiae FPL-YS1020 (pYS41) | This study |
| S. cerevisiae FPL-YS42 | S. cerevisiae FPL-YS1020 (pYS42) | This study |
| Plasmids | | |
| pRS314 | TRP1, CEN/ARS | (Sikorski and Hieter, 1989) |
| pRS424 | TRP1, 2-μm origin | (Christianson et al., 1992) |
| pYPR2831 | TRP1, 2-μm origin, GAPDH promoter and terminator | (Horiuchi et al., 1990) |
| pYS31N | XYL3 in pRS314 | (Jin et al., 2002) |
| pYS32N | XYL3 in pRS424 | (Jin et al., 2002) |
| pYS31 | TRP1, CEN/ARS, GAPDH$_P$-XYL3-GAPDH$_T$ | This study |
| pYS32 | TRP1, 2-μm origin, GAPDH$_P$-XYL3-GAPDH$_T$ | This study |
| pYS41 | TRP1, CEN/ARS, GAPDH$_P$-XKS1-GAPDH$_T$ | This study |
| pYS42 | TRP1, 2-μm origin, GAPDH$_P$-XKS1-GAPDH$_T$ | This study |

Enzymes, Primers and Chemicals.

Restriction enzymes, DNA modifying enzymes and other molecular reagents were obtained from New England Biolabs (Beverly, Mass.), Promega (Madison, Wis.), Stratagene (La Jolla, Calif.) and Roche Biochemical (Indianapolis, Ind.). Reaction conditions employed were as recommended by the suppliers. All general chemicals were purchased from Sigma (St. Louis, Mo.). Primers for PCR and sequencing were synthesized by Sigma-Genosys (The Woodlands, Tex.) and Invitrogen (Carlsbad, Calif.).

Yeast Transformation.

A yeast EZ-Transformation kit (BIO 101, Vista, Calif.) or Alkali-Cation Yeast Kit (BIO 101, Vista, Calif.) was used for all yeast transformations. Integration vectors were linearized with an appropriate enzyme prior to transformation. Transformants were selected on YSC medium containing 20 g/L glucose. Amino acids were added as necessary. After transformation with pITyX3, the cells were grown for 12 hours in YPD to allow for $neo^r$ expression, and transformants selected on YPD plates containing G418.

Plasmid Construction.

Plasmids used in this study are summarized in Table 1. The pX3 (Jin et al., 2002) plasmid was digested with SmaI and BsaAI to produce a 2.0 kbp fragment, which was then inserted into the SmaI site of pUC18 to produce pUC18x3. The orientation of XYL3 in pUC-X3 was confirmed by cutting the plasmid with SacI. pYS32 was constructed by inserting the 2.0 kbp EcoRI-SalI fragment from pUCl 8-X3 into pYPR2831 (Horiuchi et al., 1990). For construction of the single copy vector, pYS31, containing XYL3 with the GADPH promoter, pYS32 was digested with HindIII. The resulting 3.2 kbp HindIII-HindIII fragment was blunt-ended with T4 DNA polymerase and inserted into the SmaI site of pRS314 (28). The pYS41, containing XKS1 with GAPDH promoter, was constructed by inserting 3.3 kbp blunt-ended Hind III-HindIII fragment from pY2XK (Jin et al., 2000) into the SmaI site of pRS314. Because the XKS1 gene contains a HindIII site in the open reading frame between GAPDH promoter and terminator, the 3.3 kbp HindIII-HindIII from pY2XK was obtained by partial digestion. To construct a vector for the tunable expression of XYL3, pX3 was digested with PstI to produce a 2.9 kbp PstI-PstI fragment containing PsXYL3. The 2.9 kbp PstI-PstI fragment was inserted into the PstI site of pITy4 (Parckh et al., 1996) to produce the pITyX3.

Preparation of Crude Extract and Enzyme Assay.

S. cerevisiae was grown to exponential phase in YSC medium supplemented with appropriate amino acids and nucleotides and 20 g/L of glucose or 40 g/L of xylose. Cells were pelleted by centrifugation, and was washed and suspended in buffer (100 mM of phosphate buffer, 1 mM EDTA, 5 mM β-mercaptoethanol, pH 7.0). The suspended cells were mixed with glass beads (Sigma, St. Louis, Mo.), vortexed at maximum rate in bursts of 30 to 120 s, and then cooled on ice for a similar period. This procedure was repeated for up to ten minutes of vortexing with periodic microscopic examination to determine cell breakage. The crude extract, collected after centrifugation for ten minutes at 15000 g, was used for the enzyme assay. Xylulokinase activity was measured according to the method of Shamanna and Sanderson (Shamanna and Sanderson, 1979). A photodiode array spectrophotometer (Hewlett Packard, Wilmington, Del.) was used to monitor the reaction by absorbance at 340 nm. All assays were performed within 2 to 4 hours of cell breakage. One unit of xylulokinase activity is defined as the amount of enzyme that phosphorylates 1 μmol of xylulose per minute at 30° C. Protein concentration was determined by the BCA method (Pierce, Rockford, Ill.).

Cell Growth Experiments.

For growth on plate, cells were grown on YSC drop out (Leu⁻, Trp⁻, Ura⁻) medium with glucose, and then the cells were harvested and washed. Cells were suspended with double distilled $H_2O$ to reach $OD_{600}=10$. The cell suspension was serially diluted and plated on the YSC plate with glucose and xylose. The plates were incubated at 30° C. until colonies grew. For the growth rate measurement, cells were grown in 50 ml of YSC dropout medium with 40 g/L of xylose in 125 ml Erlenmeyer flask shaken at 200 rpm. Initial cell growth (less than $OD_{600}<2$) was used for calculation of specific growth rate.

Metabolic Flux Calculation.

Metabolic fluxes of the xylose assimilation steps were calculated from the xylose consumption rates, and the xylitol and xylulose accumulation rates during initial xylose fermentation within 24 hours. By assuming that no accumulation of xylose, xylitol, and xylulose in the cell, metabolic fluxes were calculated by following equations.

$$J_{XYLOSE}=J_{XYLITOL}+J_{XDH} \quad \text{(Equation 1)}$$

$$J_{XYLULOSE}=J_{XDH}-J_{XK} \quad \text{(Equation 2)},$$

where $J_{XYLOSE}$, $J_{XYLITOL}$, $J_{XYLULOSE}$ represent specific rate of xylose consumption, xylitol accumulation, and xylulose accumulation and $J_{XDH}$ and $J_{XK}$ represent internal fluxes of XDH and XK reaction.

Quantitative PCR for Determining Copy Number of XYL3 in the Cell.

Genomic DNA from S. cerevisiae FPL-YSX3 and Pichia stipitis CBS6054 was isolated as described in Rose et al. (Rose et al., 1990). S. cerevisiae FPL-YSX3 is a select recombinant made by introducing the XLY3 gene into S. cerevisiae FPL-YS1020 using pITyX3, as described below. Genomic DNA was extracted three times with an equal volume of phenol:cholorform:isopropyl alcohol (25:24:1). The DNA was precipitated using one-half volume of ammonium acetate and two volumes of 100% ethanol, and resuspended in TE (10 mM Tris-HCl, pH 8.0, 1 mM EDTA). The concentration and purity of DNA was determined using a GeneQuant. (Pharmacia Biotech). Quantitative PCR primers were designed to XYL1 (5'-GATACCTTCGTCAATGGC-CTTCT-3' (SEQ ID NO:1) and 5-TTCGACGGTG CCGAAGA-3), (SEQ ID NO:2), XYL2 (5'-TTCGACGGT-GCCG-AAGA-3' (SEQ ID NO:3) and 5'GATACCT-TCGTCA ATGGCCTTCT-3' (SEQ ID NO:4)), and XYL3 (5'-GAAGGTGACATTGCCTCTTACTTTG-3' (SEQ ID NO:5), and 5'-TCCGGTGAACGAGTAGATTTTACA-3' (SEQ ID NO:6)) using Primer Express software (Applied Biosystems). Quantitative PCR was performed using SYBR® Green PCR Master Mix (Applied Biosystems) and a 7000 ABI PRISM 7000 Sequence Detection System (Applied Biosystems). Quantification was performed using the standard curve method (De Preter et al.). Standard curves for XYL1, XYL2, and XYL3 were constructed and the copy numbers of the genes were interpolated using these standard curves. 1.6, 0.4, 0.1, 0.025 and 0.00625 ng of P. stipitis genomic DNA was used to construct a standard curve for each of the three genes. Quantitative PCR conditions were as recommended by the manufacturer except that half the reaction volume was used: 50° C. for 2 min, 95° C. for 10 min, and 40 cycles of 95° C. for 15 s and 60° C. for 1 min; 7.5 pmoles of each primer. The standard curve was then used to determine equivalents of each of these genes in three dilutions of genomic DNA from FPL-YSX3. All reactions were performed in triplicate.

Statistical Analyses.

Statistical analysis of quantitative PCR data was performed by using Excel (Microsoft Corporation, Redmond, Wash.). For pair-wise comparisons of the copy numbers, two-sided t tests were used to determine if the copy numbers are the same with the null hypothesis ($H_0$: $\mu_{XYL1}=\mu_{XYL2}$, $H_0$: $\mu_{XYL1}=\mu_{XYL3}$, and $H_0$: $\mu_{XYL2}=\mu_{XYL3}$). For the calculation of the copy number of XYL3, linear regression was performed with the following model:

$$Y_i=c_1x_i+e_i \quad \text{(Equation 3)}$$

where Y and x represent the amount of XYL3 and XYL1 in the genomic DNA, respectively. $e_i$ corresponds to the error of the regression and $c_1$ indicates the copy number of XYL3 when we assume that the copy number of XYL1 is one.

Analytical Methods.

Glucose, xylose, xylitol, xylulose and ethanol concentrations were determined by HPLC (HP, Wilmington, Del.) with an ION 300 column (Interaction Chromatography, San Jose, Calif.). Cell growth was monitored by optical density at 600 nm ($OD_{600}$). One $OD_{600}$ at 600 nm was equivalent to 0.17 g cell/L for S. cerevisiae.

Culture Conditions for Evaluating Differential Gene Expression.

S. cerevisiae FPL-YSX3 (MATα, leu2::LEU2-XYL1, ura3::URA3-XYL2, Ty3::NEO-XYL3) was grown in YP medium with the appropriate carbon source. Cells were grown in four different culture conditions, i.e. two dissolved oxygen levels (oxygen-limited, aerobic) with each carbon source (glucose or xylose) as summarized in Table 2. For the aerobic condition, cells were cultured in 200 ml of YP medium with either 20 g/L of glucose or xylose in 1000 ml flasks shaken at 300 rpm. Cells were harvested at OD=1 in order to avoid oxygen limitation. For the oxygen limited condition, cells were cultivated in 50 ml of YP medium with either 40 g/L of glucose or xylose in 125 ml flasks shaken at 100 rpm. Cells were harvested at OD=30 to induce oxygen limitation. Residual sugar concentrations were determined by HPLC to prevent the depletion of carbon source. Cells from culture were harvested as quickly as possible. Cell pellets were washed once in sterilized water and placed in liquid nitrogen for a least one minute. Frozen cell pellets were kept at −80° C. until RNA extraction.

TABLE 2

| Summary of experimental conditions | | |
|---|---|---|
| Conditions | Glucose | Xylose |
| Aerobic | 2% Glucose (G/A) | 2% Xylose (X/A) |
| Oxygen-limited | 4% Glucose (G/OL) | 4% Xylose (X/OL) |

RNA Isolation and Purification.

Prewarmed 3 ml aliquots of acid phenol-chloroform-isoamyl alcohol (125:24:1, pH 4.7) and 3 ml aliquots of TES buffer (10 mM Tris, pH 7.5, 10 mM EDTA, 5 g/L of SDS) were added to frozen cell pellets and incubated at 65° C. with 20 seconds vortexing every 10 minutes. Total RNA was isolated by additional acid phenol-chloroform-isoamylalchohol extraction and subsequent extraction by chloroform: isoamyl alcohol (24:1). Isolated RNA was precipitated by adding 1/10 volume of 3 M sodium acetate (pH 5.2) and 2 volumes of 100% precooled ethanol. The precipitated RNA pellet was washed with 80% ethanol and dried. DEPC treated water was used for resuspension of the RNA pellet. The isolated RNA was purified further by using RNeasy kit (Qiagen Inc., Chatsworth, Calif.) according to manufacturer's instructions. After cleanup, the A260/A280 was checked to ensure the purity of RNA.

cDNA Synthesis from Total RNA.

For first strand cDNA synthesis, 1 µL of T7-d(dT)24 primer (100 pmol/µL, GENSET Corp): 5'-GGCCAGT-GAATTGTAATACGACTCATATAGGGAGGCGG-(dT) 24-3' (SEQ ID NO:7) and 40 µg of total RNA were incubated at 70° C. for 10 minutes and subsequently 4 µL of 5× first strand cDNA buffer (250 mM Tris-HCl (pH 8.3), 375 mM KCl, 15 mM $MgCl_2$), 2 µL of 0.1 M DTT, and 1 µL of 10 mM dNTP mix were added. After 2 minutes of incubation at 42° C., 5 µL of Superscript II (200 U/µL, Gibco) was added and incubated at 42° C. for 1 hour. Second strand cDNA synthesis was performed as follows:

Reaction mixtures included 20 µL of first cDNA synthesis reaction, 91 µL of DEPC-treated water, 30 µL of 5× second strand reaction buffer (100 mM Tris-HCl (pH 6.9), 450 mM KCl, 23 mM $MgCl_2$, 0.75 mM β-$NAD^+$, 50 mM $(NH_4)_2SO_4$), 3 µL of 10 mM dNTP, 1 µL of DNA ligase (10 U/µL), 4 µL of DNA Polymerase I (10 U/µL), and 1 µL of RNase H (2 U/µL). The reaction mixture was incubated at 16° C. for 2 hours. Then 2 µL of T4 DNA Polymerase (5 U/µL) was added to each reaction and incubated for 5 minutes at 16° C. The reaction was terminated by adding 10 µL of 0.5 M EDTA. The cDNA was purified by phenol:chloroform:isoamyl alcohol (25:24:1, saturated with 10 mM Tris-HCl pH 8.0) extraction and precipitated by adding 0.5 volumes of 7.5 M ammonium acetate with 2.5 volumes of absolute ethanol.

RNA Transcript Labeling by In Vitro Transcription (IVT)

For the production of large amounts of hybridizable biotin-labeled RNA transcript, a BioArray kit (Enzo) was used according to manufacturer's instruction. 1 µg of cDNA was used for template DNA of IVT reaction. From the IVT reaction mixture, biotin-labeled RNA transcript (cRNA) was purified by RNeasy spin column (Qiagen Inc., Chatsworth, Calif.) according to cleanup protocol provided by manufacturer. Purified cRNA then was quantified by measuring $A_{260}/A_{280}$.

Fragmenting cRNA for Hybridization

The cRNA was fragmented to obtain fragments of the appropriate size for hybridization studies, described below. About 40 µg of cRNA was added into 6 µL of 5× fragmentation buffer (200 mM Tris-acetate, pH 8.1, 500 mM potassium acetate, 150 mM magnesium acetate) with appropriate amounts of RNase-free water to make final volume of 30 µL. The fragmentation reaction was incubated at 94° C. for 35 minutes. 1 µL of fragmented cRNA was run on a 10 g/L of agarose gel to evaluate the size distribution.

Hybridization, Staining and Scanning.

Hybridization and scanning were performed in Genome Center of Wisconsin (GCOW), which is equipped with the GeneChip™ Instrument System. The integrity of labeled probe was tested with a Test3 array (Affymetrix, Santa Clara, Calif.). For main hybridization, a S98 yeast oligonucleotide array (Affymetrix, Santa Clara, Calif.) was used for hybridization. Hybridization, staining, and scanning were done according to manufacturer's protocols.

Monitoring Expression Levels of XYL1, XYL2, and XYL3.

Because the Affymetrix Yeast S98 chip does not contain probes for monitoring XYL1, XYL2, and XYL3 from P. stipitis, quantitative RT-PCR technology was used to monitor these genes. Genomic DNA contamination in RNA was checked by PCR. To test for the presence of genomic DNA in the final volume of cDNA, the actin gene was amplified using a primer complementary to the intron of this gene (5'-CTGTAAGAAGAATTGCACGGTCCC'-3') (SEQ ID NO:8) and to the middle of the open reading frame (5'-TCAAAATGGCGTGAGGTAGAGA-3) (SEQ ID NO:9). The PCR conditions were 94° C. for 5 min; 30 cycles of 94° C. for 30 s, 55° C. for 30 s, 72° C. for 1 min; and 72° C. for 5 min. Taq Polymerase (Promega) was used. 1 µl of each cDNA reaction was used as template. When 1 µl of cDNA reaction was used as a template, no amplified product was visualized by gel electrophoresis and staining with ethidium bromide. In contrast, when 2 µl or 0.02 ng of genomic DNA was a template, a DNA fragment was amplified.

mRNA Abundance Calculations.

mRNA copy number per cell was calculated using the hybridization signal obtained from GeneChip software (Affymetrix, Santa Clara, Calif.). We assumed that 15,000 mRNA molecules per cell exist in yeast (Hereford and Rosbash, 1977). The fraction of each gene from the total hybridization signal was multiplied by 15,000/cell to give the copy number per cell. For the calculation of mRNA copy numbers of XYL1, XYL2, and XYL3, the relative abundance of XYL1, XYL2, and XYL3 was compared to ACT1 by quantitative RT-PCR. The ACT1 abundance was used to normalize the data between the GeneChip experiment and the RT-PCR result.

Data Analysis and Databases.

The DNA-Chip Analyzer (dChip) program was used to analyze data from the GeneChip instrument (Affymetrix, Santa Clara, Calif.). For easier data mining, we constructed a relational database between GeneChip data and other on-line databases, such as the *Saccharomyces* genome database, the Proteome database (Hodges et al., 1998), and the Comprehensive Yeast Genome Database at MIPS. Hierarchical clustering analysis and visualization were performed by using the Cluster and Treeview programs, which were developed by Eisen et al. (Eisen et al., 1998).

Induction and Isolation of Respiration Deficient Mutant

A respiration deficient mutant showing a petite phenotype was obtained by treating a culture of FPL-YSX3 cells ($10^7$ cells/mL) with 20 µg/mL ethidium bromide in YPD. The culture was wrapped with aluminum foil at 30° C. for 24 hours. Cells were cultivated again in YPD with EtBr to ensure induction of respiration mutant and plated on YPD agar plates. A petite mutant was selected and designated YXS3P. Following isolation, respiration activity was evaluated using a Clark oxygen electrode, and the absence of respiration activity confirmed.

Fermentation Experiment

*S. cerevisiae* FPL-YSX3 and the petite mutant FPL-YSX3P were grown on YPD medium at 30° C. Cells were harvested and inoculated into 50 ml of YP with sugar mixture (10 g/L of glucose and 20 g/L of xylose) or with xylose (40 g/L) in 125 Erlenmeyer flasks shaken 100 rpm. Fermentations were performed in triplicate.

RESULTS

Construction of Recombinant *S. cerevisiae* Expressing Different Levels of XYL3 and XKS1 in a Background with Integrated XYL1 and XYL2.

To investigate the relationship between the levels of XK activity and xylose fermentation, recombinant *S. cerevisiae* strains were constructed with different XK activities. FPL-YS1020, which contains single chromosome-integrated copies of XYL1 and XYL2 driven by the ScGAPDH promoter (ScGAPDHp), was used as the host strain for expression of XYL3 and XKS1. Gene expression levels were altered by changing the promoters and the plasmid copy number. ScGAPDHp served as a strong promoter and the native XYL3 promoter was used as a weak promoter. For copy number control, either a multi copy or single copy plasmid harbored the expression cassettes (Table 3). FPL-YS1020 cells transformed with the plasmids were grown on glucose and xylose, and XK activities were measured. The XK activity of transformants varied according to copy number, promoter strength and the carbon source. Generally, XK activity increased along with copy numbers and promoter strength (Table 3). FPL-YS32, which contains XYL3 under control of ScGAPDHp in a multi copy vector, showed the highest XK activity in the cells both grown on glucose and xylose (31.35±2.24 U/mg and 9.99±0.76, respectively). Transformants containing *P. stipitis* XYL3 showed higher XK activity than those containing *S. cerevisiae* XKS1, although the same plasmids and promoters were used. XK activity in control strains increased when cells were grown on xylose as compared to the cells grown on glucose, which suggests that expression of endogenous XKS1 is induced by xylose (Table 3). Expression of genes driven by ScGAPDHp increased significantly when cells were grown on glucose.

TABLE 3

Xylulokinase activity in the recombinant strains

| Strains | Specific xylulokinase activity (U/mg) ± Error[a] | |
| --- | --- | --- |
| | Glucose | Xylose |
| Control[b] | 0.06 ± 0.01 | 0.21 ± 0.08 |
| FPL-YSX3 | 0.63 ± 0.10 | 0.67 ± 0.11 |
| FPL-YS31N | 0.18 ± 0.01 | 0.30 ± 0.15 |
| FPL-YS32N | 1.53 ± 0.05 | 0.33 ± 0.23 |
| FPL-YS31 | 6.11 ± 0.33 | 3.45 ± 0.66 |
| FPL-YS32 | 31.35 ± 2.24 | 9.99 ± 0.76 |
| FPL-YS41 | 0.13 ± 0.01 | 0.32 ± 0.04 |
| FPL-YS42 | 0.77 ± 0.07 | 1.27 ± 0.01 |

[a]Values are averages of data from two independent experiments. Error represents deviation of each data from average.
[b]The control represents the average of the values from three strains containing control vectors (pRS314, pRS424, and pYPR2831) expressed in FPL-YS1020.

Effect of Xylulokinase Activity on Recombinant *S. cerevisiae* Growth.

Growth rates of transformants that showed different levels of XK were tested on agar plates of YSC drop out medium with glucose or xylose as the sole carbon source (FIG. 1). With reference to FIG. 1, 'S' and 'M' denotes single-copy or multiple copies of the XK gene, respectively; 'N' and 'G' denote native or GAPDH promoters, respectively. The specific growth rate on xylose is expressed in $h^{-1}$. The levels of XK activity did not affect growth on glucose. All of the transformants grew as well as the control strains when glucose was the carbon source. However, the FPL-YS32, FPL-YS42, and FPL-YS32N transformants, which showed relatively higher XK activity when tested following growth in liquid medium, grew slowly on xylose. The greatest growth inhibition was observed with FPL-YS32, which showed the highest XK activity. Note that similar numbers of colonies were observed with various strains when grown on glucose, whereas smaller and fewer colonies were observed when high XK strains were plated on xylose (FIG. 1). Higher expression of either of the XK genes (XKS1 or XYL3) was deleterious to cell growth. Regardless of the origin, overexpression of an XK gene (XYL3 or XKS1) in *S. cerevisiae* is toxic to cells grown on xylose.

Effects of Xylulokinase Levels on Xylose Fermentation by Recombinant *S. cerevisiae*.

Figure 3:
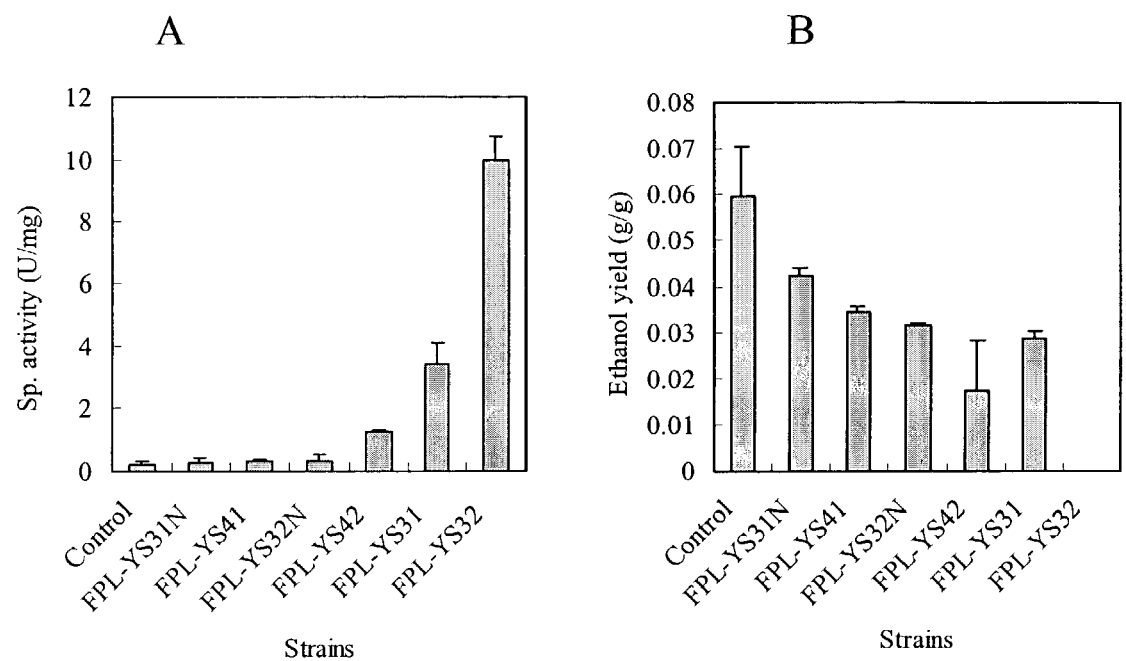
FIG. 3 shows differences between recombinant strains of *S. cerevisiae* with respect to xylulokinase specific activity (A) and ethanol yields (B).

Transformants (FPL-YS31, FPL-YS32, FPL-YS31N, FPL-YS32N, FPL-YS41, and FPL-YS42) with the XYL3 or XKS1 gene either under the control of ScGAPDHp or the native *P. stipitis* promoter in either multi-copy or single copy were first grown on the YSC dropout medium with 20 g/L of glucose. Cells were harvested and inoculated into 50 ml of YSC dropout medium with 40 g/L of xylose in 125 ml Erlenmeyer flasks shaken at 200 rpm. FIG. 2 shows the profiles of cell mass, xylose consumption, ethanol production, xylitol production of yeast strains during xylose fermentation: FPL-YS31 ( ), FPL-YS32 ( ), FPL-YS41 (Δ), FPL-YS42 (▲), and control ( ) (FPL-YS1020 containing the corresponding plasmid without XYL3). As discussed above, FPL-YS32 did not grow as well as the other strains when cultivated in xylose liquid medium. However, in contrast to the plate experiments, FPL-YS31, FPL-YS41, and FPL-YS42 grew slightly better than the control strains when each was cultivated in xylose liquid medium. The slowest grower, FPL-YS32, also consumed xylose slowest and did not produce ethanol. FPL-YS31, FPL-YS41, and FPL-YS42 consumed xylose faster but accumulated more xylitol than control strains. Interestingly, ethanol production decreased with increasing XK activity in recombinant *S. cerevisiae*. Ethanol yields from xylose are presented along with enzymatic activities in the FPL-YS31, FPL-YS32, FPL-YS31N, FPL-YS32N, FPL-YS41, and FPL-YS42 transformants (FIG. 3). The results showed an inverse relationship between ethanol yield and XK activity during xylose fermentation.

Tunable Expression of XYL3 in the Recombinant *S. cerevisiae* FPL-YS1020.

The results presented above indicate that overexpression of XK is deleterious to the cell when xylose is the sole carbon source. However, previous studies (Honansson et al., 2001; Toivari et al., 2001, Ho et al., 1998) reported that overexpression of *S. cerevisiae* XKS1 enhances xylose fermentation by recombinant *S. cerevisiae* containing XYL1 and XYL2. Recombinant *S. cerevisiae* expressing only XYL1 and XYL2 accumulate xylulose during xylose fermentation (Jin and Jeffries, 2002).

We inferred from these results that growth is inhibited if the expression level of XK is too high, and if XK expression levels are too low, cells cannot maintain flux for efficient xylose assimilation. Therefore, we attempted to bypass these problems by optimizing the expression level of XYL3 using a tunable expression vector (Parekh et al., 1996), which uses a yeast transposon (Ty, δ) element (Boeke et al., 1985) in the chromosome as an insertion site. It is possible to obtain transformants with multiple integration of the vector because more than several hundred copies of Ty are present in the yeast genome (Kingsman and Kingsman, 1988). Multiple integration would give rise to higher levels of gene expression because expression is essentially a linear function of copy number. XYL3 was introduced into FPL-YS1020 using pITyX3, which contains a Ty3 element, the G418 resistance gene (neo), and XYL3. pITyX3 was linearized by cutting with XhoI and transformed into FPL-YS1020. Putative transformants were selected on YPD containing 300 μg/mL of G418. pITyX3 could integrate into the *S. cerevisiae* chromosome at multiple sites. Because the location and copy number of pITyX3 in the chromosome could affect the expression of XYL3, 40 independent transformants were tested in single trials for growth on xylose. Relative growth was calculated by dividing the cell density of a transformant culture by the cell density of a parental strain. FIG. 4A shows the growth of the various transformants as a histogram in which the relative cell growth is plotted versus the frequency of its occurrence. The fastest growing strain and eight other strains were examined in a fermentation trial. As expected, each transformant also showed significantly different ethanol production from xylose (FIG. 4B). The best strain (No. 25) was selected based on its product yield, and designated FPL-YSX3. XK activity in FPL-YSX3 was found to be much higher than the parental strain, FPL-YS 1020 (Table 3).

Copy Number Determination of XYL3 in FPL-YSX3 Strain.

The copy numbers of XYL1, XYL2, and XYL3 in FPL-YSX3 were determined using quantitative PCR, which offers a wide dynamic range of quantification with high accuracy (De Preter et al., 2002; Ingham et al., 2001, Bieche et al., 1998). Because AYL1 and XYL2 were inserted into FPL-YSX3 by site-specific integration, a single copy per haploid genome can be assumed. By comparing the copies of XYL3 present in 0.2, 0.1, and 0.05 ng DNA to the copies of XYL1 and XYL2 present, the number of copies of XYL3 per genome was calculated. For a standard curve, genomic DNA of P. stipitis was used because it contains XYL1, XYL2, and XYL3 in a single copy. For AYL1 and XYL2, 0.275±0.77 and 0.207±0.082 equivalents per genome were found, respectively. The copy number of XYL1 and XYL2 were similar (P>0.05). In contrast, XYL3 was found at 1.095±0.348 equivalents per genome, which was significantly different from XYL1 and XYL2 (P<0.001 for both). Because XYL1 and XYL2 are each present in a single copy in the haploid genome, the copy number of XYL3 was calculated in the interval of 3.67±1.30 copies per genome, with a 95% confidence.

Comparison of Metabolic Fluxes in FPL-YS1020 and FPL-YSX3.

Figure 5:
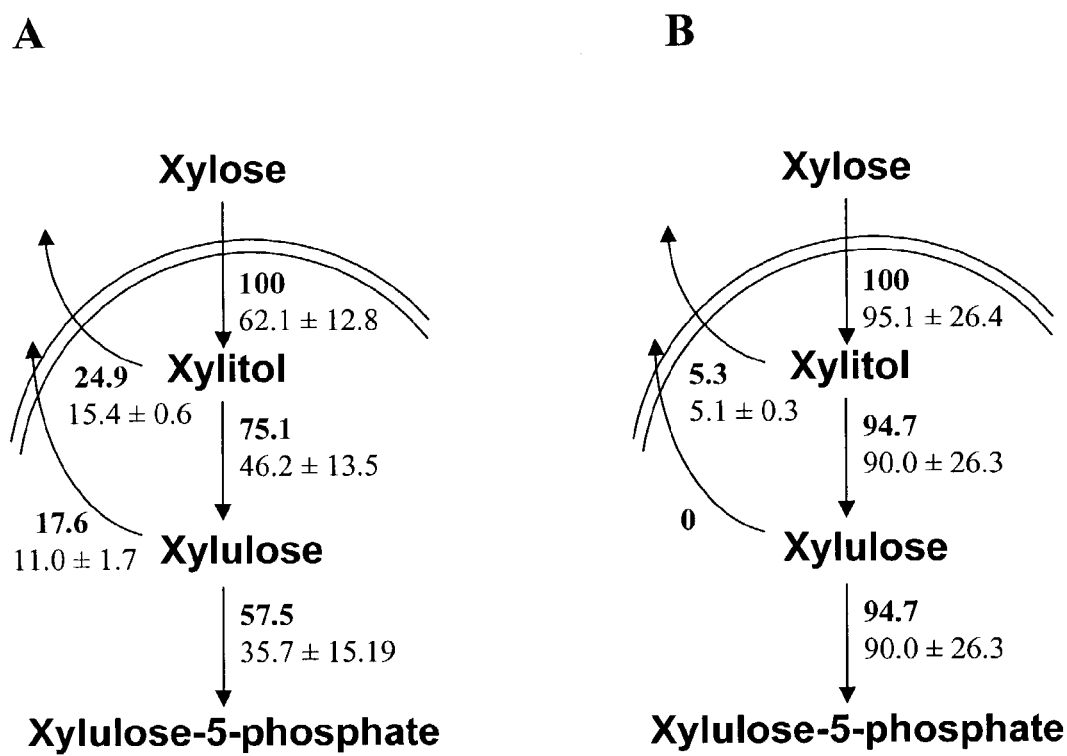
FIG. 5 shows the metabolic flux distributions of recombinant *S. cerevisiae* FPL-YS1020 (A) and FPL-YSX3 (B).

Fluxes of metabolites in the xylose assimilation steps were calculated from the xylose consumption rates, and the xylitol and xylulose accumulation rates of three independent batch fermentations by FPL-YS1020 (FIG. 5A) or FPL-YSX3 (FIG. 5B) in YP with xylose (40 g/L) at an oxygen transfer rate of 4.3 mMO$_2$/h. The fluxes are presented as the average±SD in μmol (g cell h)$^{-1}$. Metabolic flux distributions changed drastically after introduction of XYL3. Xylose consumption increased 1.7-fold and xylitol accumulation decreased 3-fold after expression of XYL3 in FPL-YS1020. Moreover, xylulose accumulation was not observed. This result shows that an appropriate level of XK is important for efficient xylose utilization by recombinant S. cerevisiae.

Comparison of Xylose Fermentation by Recombinant S. cerevisiae in YP Medium with Xylose.

Xylose fermentation by L2612, FPL-YS10, FPL-YS1020, and FPL-YSX3 were compared. L2612 was the parental strain used for further engineering of xylose metabolism (Cho et al., 1999). FPL-YS10 has only XYL1, and FPL-YS1020 contains XYL1 and AYL2 (Jin and Jeffries, 2002). FPL-YSX3 contains XYL1, XYL2, and XYL3. YP medium with 20 g/L of xylose was used for fermentation experiments. As shown in Table 4, the parental strain FPL-YS 10 did not consume significant amounts of xylose (less than 1 g/L). FPL-YS1020 consumed 8 g/L of xylose, but half of the consumed xylose was converted into xylitol (3.93 g/L). Ethanol production by FPL-YS1020 was not significant (less than 1 g/L). However, FPL-YSX3 consumed xylose much faster than other strains and produced ethanol with a yield of 0.12 g ethanol/g xylose. FPL-YSX3 still accumulated xylitol as a by-product, but a much lower level than lower than that observed with FPL-YS1020 (0.27 g xylitol/g xylose compared to 0.50 g xylitol/g xylose). These results clearly show that an appropriate low level of XYL3 expression increases xylose uptake and ethanol production but decreases xylitol accumulation during xylose fermentation by recombinant S. cerevisiae.

TABLE 4

Xylose consumption, xylitol and ethanol production by S. cerevisiae strains

| | L2612 | FPL-YS10 | FPL-YS1020 | FPL-YSX3 |
|---|---|---|---|---|
| Consumed xylose (g/L) | 0.37 ± 0.18[a] | 0.61 ± 0.12 | 7.9 ± 0.58 | 16.91 ± 0.44 |
| Produced xylitol (g/L) | 0.27 ± 0.03 | 0.33 ± 0.01 | 3.93 ± 0.30 | 4.56 ± 0.03 |
| Ethanol (g/L) | 0 | 0 | 0 | 1.94 ± 0.05 |
| Xylitol yield (g/g) | 0.74 ± 0.18 | 0.55 ± 0.09 | 0.50 ± 0.07 | 0.27 ± 0.01 |
| Ethanol yield (g/g) | 0 | 0 | 0 | 0.12 ± 0.01 |

[a]Displayed values are the average ± SD of three independent replicate experiments.

Xylose Fermentation by FPL-YSX3 in Minimal Medium with Xylose.

Figure 6:
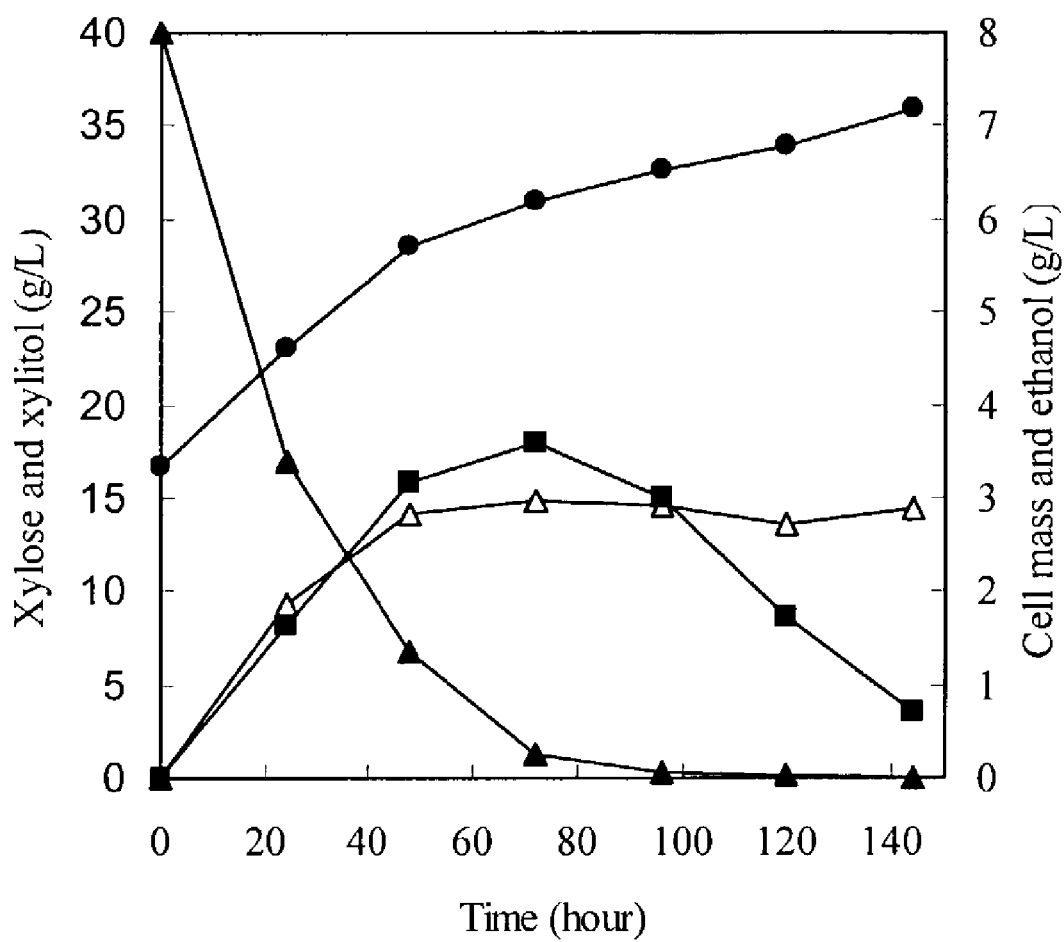
FIG. 6 shows xylose fermentation by *S. cerevisiae* FPL-YSX3 with respect to cell mass (●), ethanol (■), xylose (▲), and xylitol (Δ).

The FPL-YSX3 strain was transformed with the control vector (pYPR2831) for the comparison of growth and ethanol production from YSC medium with xylose. The cells were grown on YSC dropout medium with 20 g/L of glucose and inoculated again into 50 ml of YSC dropout medium with 40 g/L of xylose in 125 ml Erlenmeyer flasks shaken at 200 rpm. FIG. 6 shows profiles of cell mass (●), ethanol (■), xylose (▲), and xylitol (Δ). The cells grew better on xylose and consumed xylose much faster than the strains shown in FIG. 2. Maximum ethanol concentration was 3.4 g/L, which was greater than two-fold higher than that of the control strains, which do not contain XYL3. However, xylitol was still a major byproduct (13 g/L).

Overview of Transcriptional Reprogramming with Respect to Changes in Carbon Sources and Aeration.

Figure 9:
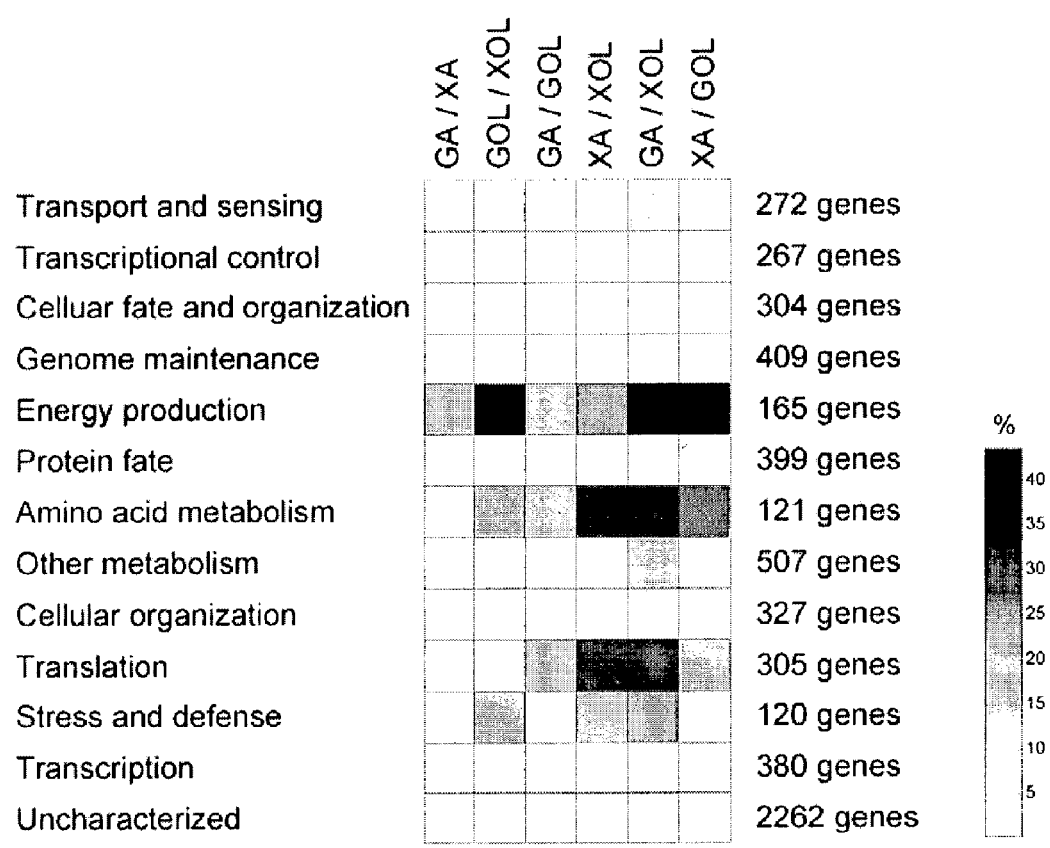
FIG. 9 shows classification of genes the expression of which is affected by changes in aeration or carbon source.
Figure 10:
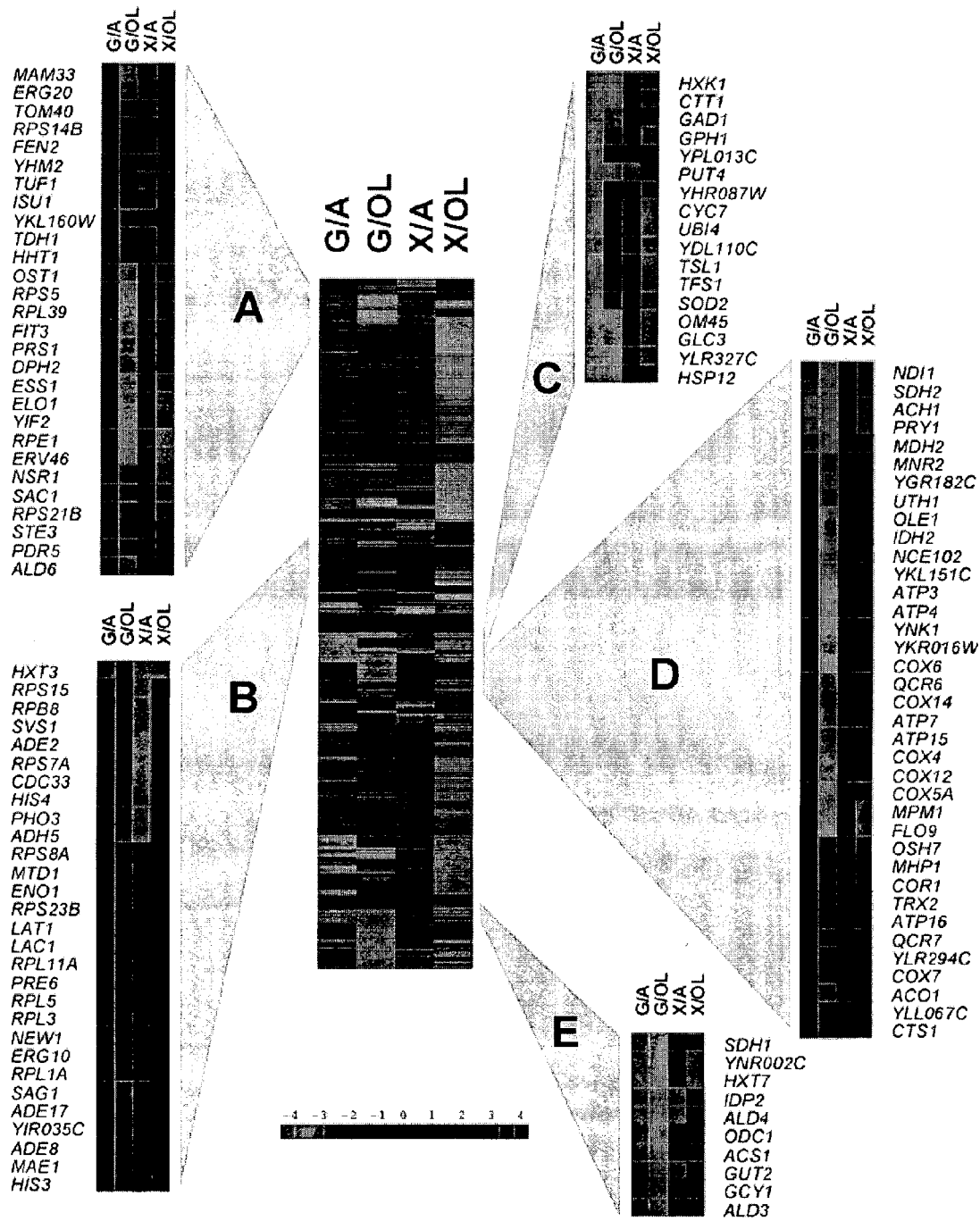
FIG. 10 shows five characteristic clusters of genes affected by changes in growth conditions, including genes induced under aerobic conditions (A), genes induced by glucose (B), and genes highly expressed during xylose metabolism (C, D, and E).

In order to identify genes differentially expressed in response to different carbon sources or aeration conditions, we filtered GeneChip data with the criteria that we obtained from replication of the control condition (Table 5). Only 5.0% of genes passing these criteria were differentially expressed during glucose metabolism between high and low aeration conditions. This suggests that oxygen does not have much control over global gene expression during glucose metabolism. In contrast, 8.7% of genes showed more than 2-fold difference in expression during xylose metabolism between the two aeration conditions. This result suggests that xylose metabolism depends greatly on oxygen availability. Transcripts that changed significantly between two out of four conditions were classified into functional categories. As expected, expression of genes involved in energy production exhibited the greatest change (FIG. 9). We identified 785 genes whose mRNA levels shifted significantly under one or more of the four conditions. The patterns in expression levels of 785 genes were clustered to reveal the genes whose expression levels were similar over four different environmental changes. FIG. 10 shows five characteristic clusters that have similar mRNA levels. Cluster A shows genes whose expression level increases during aerobic conditions regardless of the carbon source. Cluster B lists genes the expression of which is higher during glucose metabolism regardless of aeration conditions. Clusters C, D, E indicate genes that are highly expressed during xylose metabolism.

TABLE 5

Number of genes showing difference of greater than two-fold under corresponding conditions

| | | Glucose | | Xylose | |
|---|---|---|---|---|---|
| Conditions | | Aerobic (GA) | Oxygen limited (GOL) | Aerobic (XA) | Oxygen limited (XOL) |
| Glucose | Aerobic (GA) | NA | 290 (5.0%) | 136 (2.3%) | 624 (10.7%) |
| | Oxygen limited (GOL) | | NA | 396 (6.8%) | 386 (6.6%) |
| Xylose | Aerobic (XA) | | | NA | 509 (8.7%) |
| | Oxygen limited (XOL) | | | | NA |

Expression Levels of XYL1, XYL2, and XYL3 in *S. Cerevisiae*.

Figure 11:
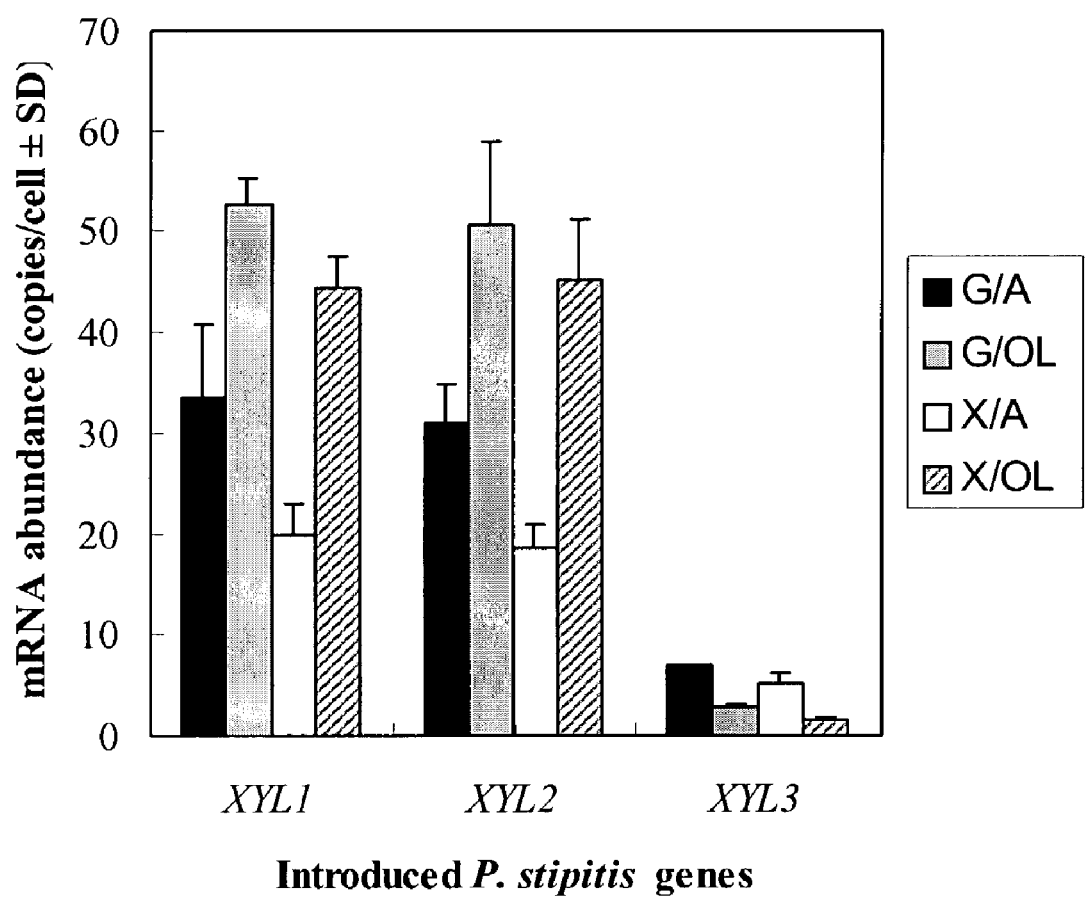
FIG. 11 shows the mRNA abundance in copies/cell of AYL1, XYL2, and XYL3 of cells grown on glucose (G) or xylose (X) with aeration (A) or under oxygen limiting (OL) conditions.

Because we could not monitor expression levels of heterologous genes using the S98 array (Affymetrix, Santa Clara, Calif.), mRNA levels of the heterologous genes XYL1, XYL2, and XYL3 from *P. stipitis* were monitored by quantitative RT-PCR. As shown in FIG. 11, XYL1 and XYL2 did not change more than three-fold. Because these two genes are under the control of the GAPDH promoter, they show similar patterns of expression under four conditions. The mRNA level of XYL3 was much lower than the mRNA levels for XYL1 and XYL2 because transcription of XYL3 was driven by its native *P. stipitis* promoter. Whereas the GAPDH promoter appears to have induced transcription of XYL1 and XYL2 under oxygen-limited conditions, reduced aeration led to the lower transcript levels for XYL3 under the control of its native *P. stipitis* promoter.

Expression Levels of Primary Energy Metabolism Genes.

Figure 12:
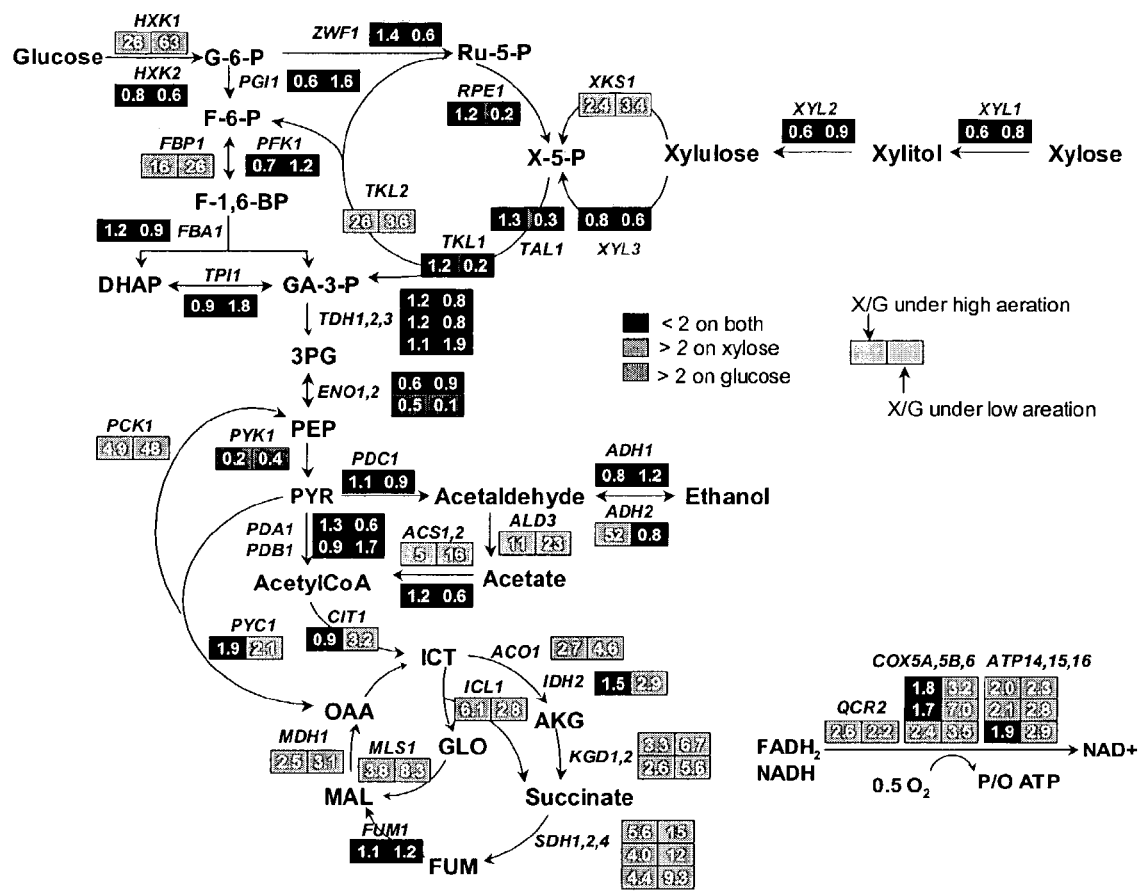
FIG. 12 shows the mRNA levels of genes involved in energy metabolism in the presence of glucose or xylose with aeration or under oxygen limiting conditions.

In order to investigate how environmental changes affect expression of genes encoding proteins responsible for primary energy metabolism, we chose the genes in the glycolysis, pentose phosphate, TCA cycle and respiration pathways and compared the mRNA levels under four experimental conditions (FIG. 12). mRNA abundances of the genes in glycolysis did not change much as a function of carbon source or aeration conditions. Interestingly, expression of HXK1, which encodes hexokinase PI, increased significantly (more than ten fold) when cells were grown on xylose regardless of aeration conditions. This was an unexpected result, because hexokinase PI is totally unrelated to xylose metabolism. Hexokinase PI is induced when cells are grown on nonfermentable carbon sources (Herrero et al., 1995), which suggests that recombinant *S. cerevisiae* recognizes xylose as a nonfermentable carbon source. Our hypothesis that xylose does not induce the expression of fermentative enzymes did not appear to be correct because mRNA levels of PDC1 and ADH1 were quite stable throughout all four conditions. However, our hypothesis that xylose does not repress respiration appears to be valid according to mRNA levels observed from experiments. The transcription of genes encoding enzymes of the TCA cycle or respiration pathway increased during xylose metabolism, whereas transcription of those genes was strictly repressed during glucose metabolism, regardless of the aeration conditions.

We also observed increased expression of genes (GND1, RPE1, TAL1) expressing proteins involved in the pentose phosphate pathway under aerobic conditions relative to oxygen-limited conditions regardless of the carbon source.

Expression Levels of Sugar Transporters.

Xylose transport may limit xylose fermentation in recombinant *S. cerevisiae* FPL-YSX3 because, in contrast to native xylose fermenting yeast, *S. cerevisiae* FPL-YSX3 does not have high affinity for xylose transporters. Xylose is known to be transported by hexose transporters in *S. cerevisiae*, although the specificity and rate are lower than for glucose. The mRNA levels of hexose transporters were investigated. Of all known 17 hexose transporters, HXT1, HXT2, HXT3, HXT4, HXT5, HXT6, and HXT7 were differentially expressed under four conditions (Table 6). It is known that transcription of HXT1 and HXT3 are induced by high glucose concentration (Reifenberger et al., 1997). We confirmed that mRNA levels of HXT1 and HXT3 were higher in the cell during growth on glucose relative to levels of cells grown on xylose. Induced transcription of HXT2 during growth on xylose at high aeration was unexpected because HXT2 and HXT4 are known to be expressed at a low level in cells growing either in the absence of glucose or in high concentrations of glucose (Reifenberger et al., 1997). Transcription of HXT6 and HXT7 was highly derepressed in the cells grown on xylose. Derepression of HXT6 and HXT7 is usually observed when cells are grown on non-fermentable carbon sources.

TABLE 6 mRNA levels of hexose transporters under different conditions

| | | mRNA abundance (copies/cell ± Error) | | | |
|---|---|---|---|---|---|
| ORF | Gene | G/A | G/OL | X/A | X/OL |
| YHR094C | HXT1 | 9.2 ± 0.6 | 2.7 | 0.1 | 0.1 |
| YMR011W | HXT2 | 2.9 ± 0.3 | 0.2 | 7.5 | 0.9 |
| YDR345C | HXT3 | 8.2 ± 1.1 | 5.5 | 0.8 | 1.0 |
| YHR092C | HXT4 | 0.2 ± 0.0 | 1.8 | 0.1 | 0.7 |
| YHR096C | HXT5 | 0.0 ± 0.0 | 0.0 | 0.3 | 2.4 |
| YDR343C | HXT6 | 2.2 ± 0.3 | 1.9 | 31.5 | 50.6 |
| YDR342C | HXT7 | 2.8 ± 0.3 | 1.8 | 29.1 | 45.0 |

Expression Levels of Redox Shuttle in Mitochondria.

Figure 13:
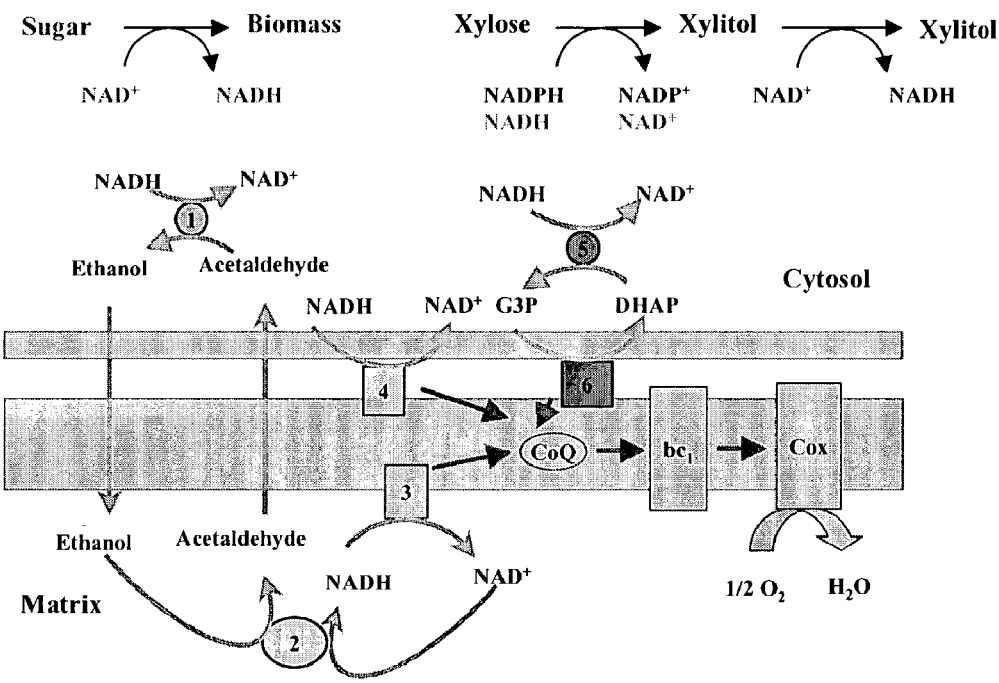
FIG. 13 shows the mRNA levels of genes in NADH/NAD shuttle of cells grown on glucose (G) or xylose (X) with aeration (A) or under oxygen limiting (OL) conditions.
Figure 13:
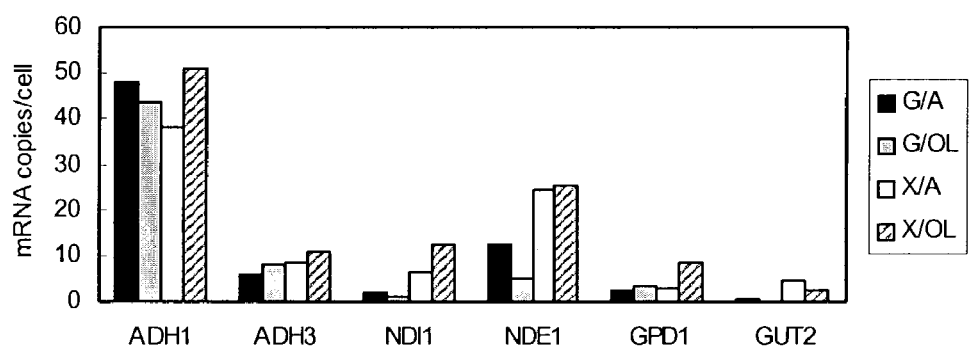

One of the main differences between glucose and xylose fermentation is cytosolic redox balance. Yeast cells can maintain a neutral redox balance in the cytosol during glucose fermentation by coupling $NAD^+$ reduction in glyceraldehyde-3-phosphate dehydrogenase (GAPDH) reaction to the ADH reaction. However, cells confront a redox imbalance during xylose fermentation because of cofactor difference in XR and XDH reaction, which causes xylitol accumulation as a byproduct. To understand how yeast responds to this imbalance during xylose metabolism, we evaluated mRNA transcript levels of known $NAD^+/NADH$ shuttle systems, including cytosolic $NAD^+$-dependent alcohol dehydrogenase (ADH1), mitochondrial $NAD^+$-dependent alcohol dehydrogenase (ADH3), mitochondrial internal NADH dehydrogenase (NDI1), mitochondrial external NADH dehydrogenase (NDE1), cytosolic $NAD^+$-dependent G-3-P dehydrogenase (GPD1), and mitochondrial flavoprotein G-3-P dehydrogenase (GUT2) (FIG. 13). mRNA levels of genes responsible for $NAD^+/NADH$ shuttle systems increased significantly during xylose metabolism. The expression of NDI1, NDE1, GPD1, and GUT1 induced during xylose metabolism. This suggests that NAD+/NADH shuttle systems are responsible for maintaining redox balance during xylose metabolism (FIG. 13).

TABLE 6 mRNA levels of hexose transporters under different conditions

| ORF | Gene | mRNA abundance (copies/cell ± Error) | | | |
|---|---|---|---|---|---|
| | | G/A | G/OL | X/A | X/OL |
| YHR094C | HXT1 | 9.2 ± 0.6 | 2.7 | 0.1 | 0.1 |
| YMR011W | HXT2 | 2.9 ± 0.3 | 0.2 | 7.5 | 0.9 |
| YDR345C | HXT3 | 8.2 ± 1.1 | 5.5 | 0.8 | 1.0 |
| YHR092C | HXT4 | 0.2 ± 0.0 | 1.8 | 0.1 | 0.7 |
| YHR096C | HXT5 | 0.0 ± 0.0 | 0.0 | 0.3 | 2.4 |
| YDR343C | HXT6 | 2.2 ± 0.3 | 1.9 | 31.5 | 50.6 |
| YDR342C | HXT7 | 2.8 ± 0.3 | 1.8 | 29.1 | 45.0 |

Expression Levels of Transcriptional Factor Hap4.

Figure 14:
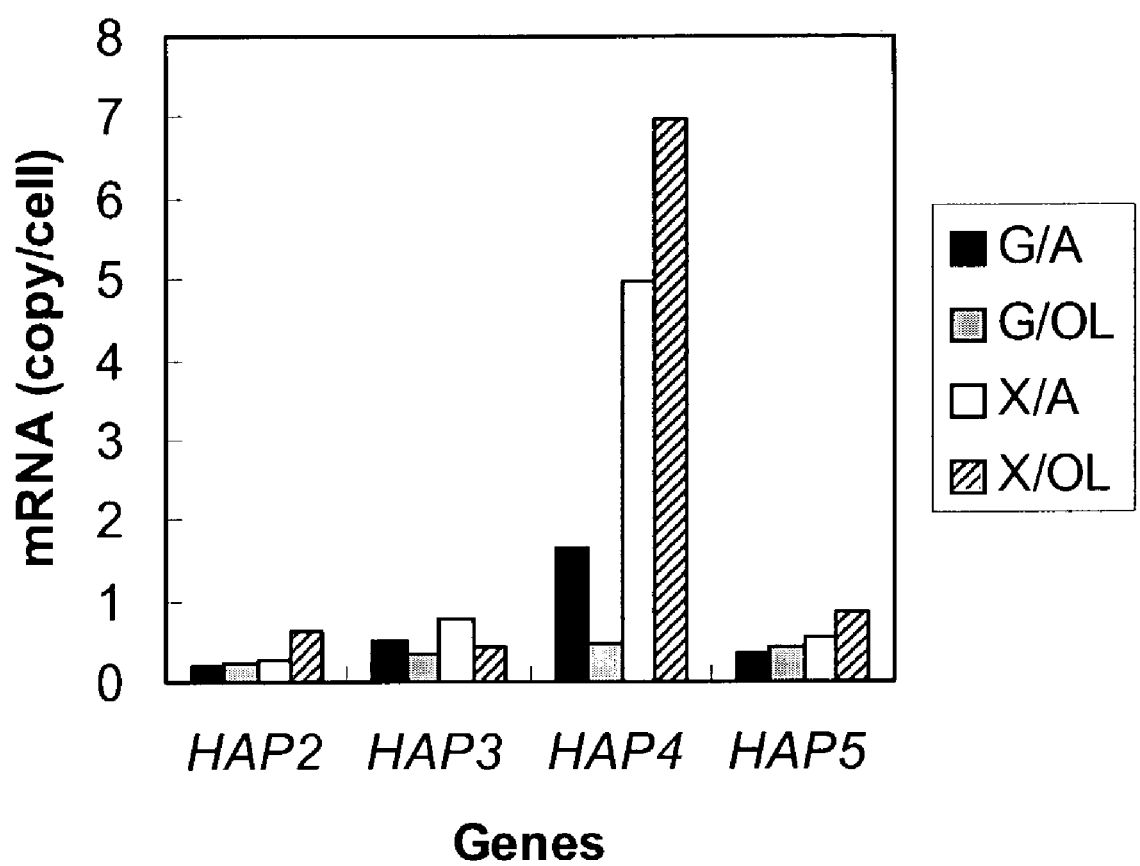
FIG. 14 shows the mRNA levels of Hap4 of cells grown on glucose (G) or xylose (X) with aeration (A) or under oxygen limiting (OL) conditions.

Transcriptional activator Hap2/3/4/5 complex is known to induce the expression of respiratory genes. When S. cerevisiae is grown on nonfermentable carbon sources, the complex binds to the so-called CCAAT box, which is usually found upstream of respiratory genes (SPR3, COX6, QCR8, and CYC1) (Olesen et al., 1987). We profiled the mRNA levels of each transcriptional factor in Hap2/3/4/5 complex under four conditions (FIG. 14). mRNA of HAP4 increased most significantly during xylose metabolism, which is consistent with previous findings that Hap4 is the main regulator of this complex (Forsburg and Guarente, 1989). This result also supports the hypothesis that the regulatory systems of S. cerevisiae treat xylose as a nonfermentable carbon source.

Induction and Isolation of Respiration Deficient Mutant.

The GeneChip experiment clearly indicated that xylose metabolism in xylose-metabolizing recombinant S. cerevisiae is oxidative because xylose did not repress expression of genes in the TCA cycle and respiration. Consequently, metabolic flux at the pyruvate branch point is not favorable for ethanol production.

Therefore, we attempted to increase the metabolic flux into ethanol production by completely blocking respiration in S. cerevisiae. Because S. cerevisiae is a petite positive yeast, a cytoplasmic petite mutant was isolated by treatment with ethidium bromide (EtBR). The respiration rates by the parental strain (FPL-YSX3) and the petite mutant (FPL-YSX3P) were measured to confirm the absence of respiration. The FPL-YSX3 consumed oxygen at the rate of $29.61 \pm 1.65$ μmol (g cell·min)$^{-1}$. However, the FPL-YSX3P did not consume a measurable amount of oxygen (data not shown). We also tested growth of petite mutant on glucose and xylose. Interestingly, FPL-YSX3P grew on glucose, but not on xylose. This result was consistent with previous observation that even xylose fermenting yeast could not grow on xylose under anaerobic conditions. Because petite cells are not capable of respiration when grown on xylose, it is evident that the limited amount of growth obtained with these cells is due to substrate level phosphorylation.

Redirecting Carbon Flux by Removing Competing Reaction.

Figure 15:
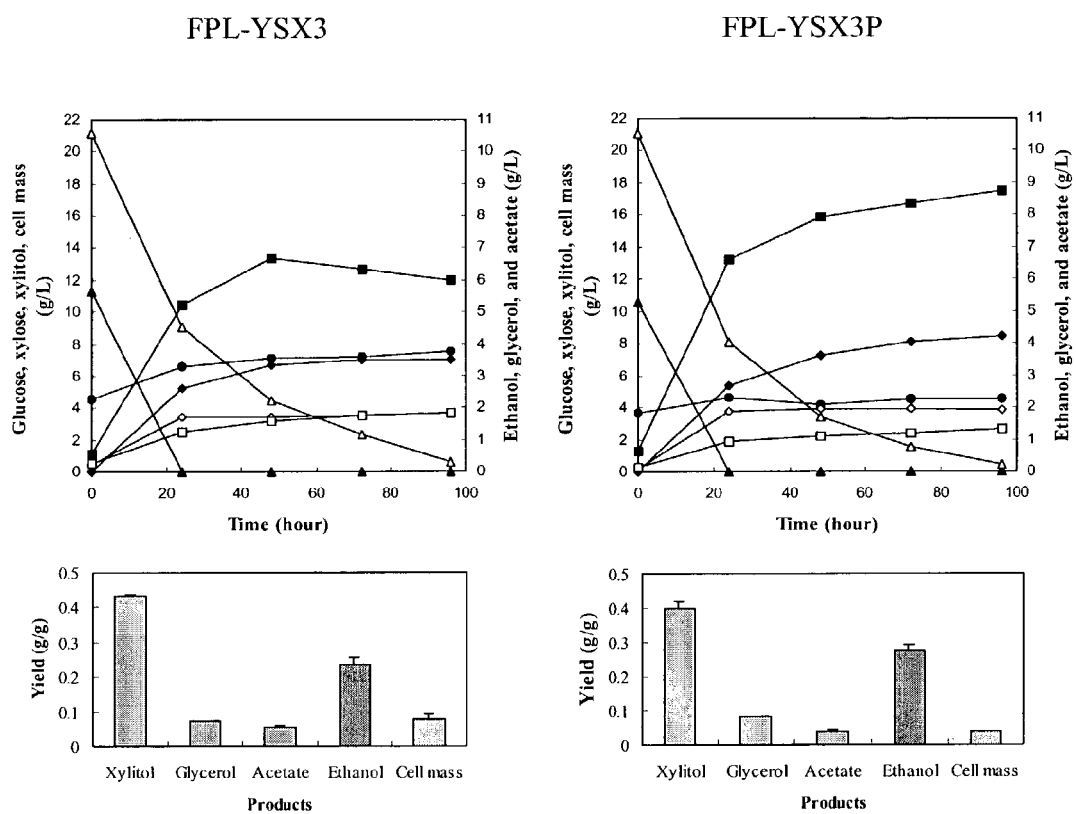
FIG. 15 compares the cell mass, acetate, ethanol, glycerol, glucose, xylose, and xylitol levels of FPL-YSX3 and FPL-YSX3P grown on xylose and glucose.
Figure 16:
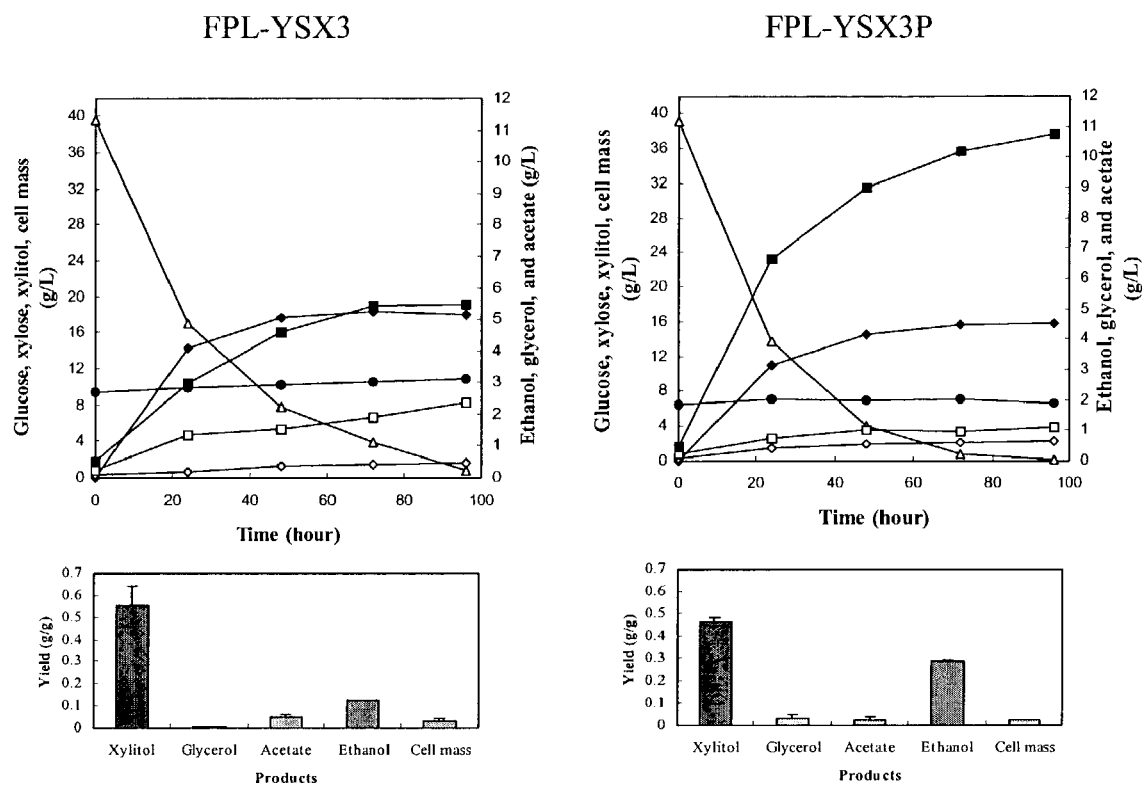
FIG. 16 compares the cell mass, acetate, ethanol, glycerol, glucose, xylose, and xylitol levels of FPL-YSX3 and FPL-YSX3P grown on xylose after first being grown on glucose.

Although the respiration deficient mutant (FPL-YSX3P) could not grow on xylose, it showed improved fermentation capacity compared to its parental strain (FPL-YSX3). As shown in FIG. 15, the FPL-YSX3P produced more ethanol from the sugar mixture of 10 g/L of glucose and 20 g/L of xylose. Maximum ethanol concentration increased 1.3 fold in FPL-YSX3 as compared to FPL-YSX3. We also performed xylose fermentation as a sole carbon source after growing the cells on glucose (FIG. 16). Specific ethanol production rate increased about three-fold in the respiration mutant as compared to the parental strain (0.013 g to 0.043 g ethanol/(g cell·h)). The mutant strain produced more ethanol and accumulated less xylitol from xylose. The maximum ethanol concentrations from 40 g/L of xylose were 5.4 g ethanol/L and 10.7 g/L for the FPL-YSX3 and the FPL-YSX3P, respectively. The ethanol yield significantly increased (from 0.12 g ethanol/g xylose to 0.29 g ethanol/g xylose) and xylitol yield slightly decreased (from 0.55 g xylitol/g xylose to 0.46 g xylitol/g xylose).

Integrating Gene Expression Data into Known Regulatory Network in Yeast.

To investigate that our expression data is compatible with known regulatory network in yeast and to summarize the data, we superimposed our expression results into a network. We retrieved a physical interaction network with 311 elements, which represent transcriptional activators and the genes of which expression is affected by the transcriptional factors. We found moderately good correlation between our expression data and the previous known network. Respiration related transcriptional activators and the genes regulated by these transcriptional factors were more expressed when cells were grown on xylose. Most transcriptional factors and genes related to amino acid synthesis are expressed more when cells were grown on glucose. In contrast, GCN4 transcript level was slightly higher on xylose than on glucose. This confirms previous findings that regulation of Gcn4 occurs at the level of translation rather than transcription. (Hinnebusch, 1997).

Each publication cited herein is incorporated by reference in its entirety.

The present invention is not limited to the exemplified embodiments, but is intended to encompass all such modifications and variations as come within the scope of the following claims.

PUBLICATIONS CITED

Bieche, I., Olivi, M., Champeme, M. H., Vidaud, D., Lidereau, R. and Vidaud, M. (1998) Novel approach to quantitative polymerase chain reaction using real-time detection: application to the detection of gene amplification in breast cancer. Int. J. Cancer. 78: 661-666.

Boeke, J. D., Garfinkel, D. J., Styles, C. A. and Fink, G. R. (1985) Ty elements transpose through an RNA intermediate. Cell. 40: 491-500.

Chiang, L.-C., Gong, C.-S., Chem, L.-F. and Tsao, G. T. (1981) D-xylulose fermentation to ethanol by S. cerevisiae. Appl. Environ. Microbiol. 42: 284-289.

Cho, K. M., Yoo, Y. J. and Kang, H. S. (1999) delta-Integration of endo/exo-glucanase and beta-glucosidase genes into the yeast chromosomes for direct conversion of cellulose to ethanol. Enzyme Microb. Technol. 25: 23-30.

Christianson, T. W., Sikorski, R. S., Dante, M., Shero, J. H. and Hieter, P. (1992) Multifunctional yeast high-copy-number shuttle vectors. Gene. 110: 119-122.

Crabtree, H. G. (1929) Observations of the carbohydrate metabolism in tumors. Biochem. J. 23: 536-545.

De Preter, K., Speleman, F., Combaret, V., Lunec, J., Laureys, G., Eussen, B. H., et al (2002) Quantification of MYCN, DDX1, and NAG gene copy number in neuroblastoma using a real-time quantitative PCR assay. Mod. Pathol. 15: 159-166.

Eisen, M. B., Spellman, P. T., Brown, P. O. and Botstein, D. (1998) Cluster analysis and display of genome-wide expression patterns. *Proc. Natl. Acad. Sci. USA.* 95: 14863-14868.

Eliasson, A., Christensson, C., Wahlbom, C. F. and Hahn-Hägerdal, B. (2000) Anaerobic xylose fermentation by recombinant *Saccharomyces cerevisiae* carrying XYL1, XYL2, and XKS1 in mineral medium chemostat cultures. *Appl. Environ. Microbiol.* 66: 3381-3386.

Epstein, C. B., Waddle, J. A., Hale, W. T., Dave, V., Thornton, J., Macatee, T. L., et al (2001) Genome-wide responses to mitochondrial dysfunction. *Mol. Biol. Cell.* 12: 297-308.

Forsburg, S. L. and Guarente, L. (1989) Identification and characterization of HAP4: a third component of the CCAAT-bound HAP2/HAP3 heteromer. *Genes Dev.* 3: 1166-1178.

Hereford, J. B. and Rosbash, M. (1977) Number and distribution of poly-adenylated RNA sequences in yeast. *Cell.* 10: 453-462.

Herrero, P., Galindez, J., Ruiz, N., Martinez-Campa, C. and Moreno, F. (1995) Transcriptional regulation of the *Saccharomyces cerevisiae* HXK1, HXK2 and GLK1 genes. *Yeast.* 11: 137-144.

Hinnebusch, A. G. (1997) Translational regulation of yeast GCN4. A window on factors that control initiator-trna binding to the ribosome. *J. Biol. Chem.* 272: 21661-21664.

Ho, N. W. Y., Chen, Z. D. and Brainard, A. P. (1998) Genetically engineered *Sacccharomyces* yeast capable of effective cofermentation of glucose and xylose. *Appl. Environ. Microbiol.* 64: 1852-1859.

Hodges, P. E., Payne, W. E. and Garrels, J. I. (1998) The Yeast Protein Database (YPD): a curated proteome database for *Saccharomyces cerevisiae*. *Nucleic Acids Res.* 26: 68-72.

Hohmann, S., Bell, W., Neves, M. J., Valckx, D. and Thevelein, J. M. (1996) Evidence for trehalose-6-phosphate-dependent and -independent mechanisms in the control of sugar influx into yeast glycolysis. *Mol. Microbiol.* 20: 981-991.

Holstege, F. C., Jennings, E. G., Wyrick, J. J., Lee, T. I., Hengartner, C. J., Green, M. R., et al (1998) Dissecting the regulatory circuitry of a eukaryotic genome. *Cell.* 95: 717-728.

Horiuchi, H., Ashikari, T., Amachi, H., Yoshizumi, M., Takagi, M. and Yano, K. (1990) High level secretion of a Rhizopus niveus aspartic proteinase in *Saccharomyces cerevisiae*. *Agric. Biol. Chem.*

Ingham, D. J., Beer, S., Money, S. and Hansen, G. (2001) Quantitative real-time PCR assay for determining transgene copy number in transformed plants. *Biotechniques.* 31: 132-134, 136-140.

Jin, Y. S. and Jeffries, T. W. (2002) Changing flux of xylose metabolites by altering expression of xylose reductase and xylitol dehydrogenase in recombinant *Saccharomyces cerevisiae*. *Appl. Biochem. Biotechnol.* in press Jin, Y. S., Jones, S., Shi, N. Q. and Jeffries, T. (2002) Molecular cloning of XYL3 (D-xylulokinase) from *Pichia stipitis* and characterization of its physiological function. *Appl Environ. Microbiol.* 68.

Jin, Y. S., Lee, T. H., Choi, Y. D., Ryu, Y. W. and Seo, J. H. (2000) Conversion of xylose to ethanol by recombinant *Saccharomyces cerevisiae* containing genes for xylose reductase and xylitol dehydrogenase from *Pichia stipitis*. *J Microbiol. Biotechnol.* 10: 564-567.

Jin, Y. S., Ni, H., Laplaza, J. M., and Jeffries, T. W. (2003) Optimal growth and ethanol production from xylose by recombinant *Saccharomyces cerevisiae* require moderate D-xylulokinase activity. *Appl. Environ. Microbiol.* 69:495-503.

Johansson, B., Christensson, C., Hobley, T. and Hahn-Hägerdal, B. (2001) Xylulokinase overexpression in two strains of *Saccharomyces cerevisiae* also expressing xylose reductase and xylitol dehydrogenase and its effect on fermentation of xylose and lignocellulosic hydrolysate. *Appl. Environ. Microbiol.* 67: 4249-4255.

Kingsman, A. J. and Kingsman, S. M. (1988) Ty: A retroelement moving forward. *Cell.* 53: 333-335.

Kötter, P. and Ciriacy, M. (1993) Xylose fermentation by *Saccharomyces cerevisiae*. *Appl. Microbiol. Biotechnol.* 38: 776-783.

Kurtzman, C, P. (1994) Molecular taxonomy of the yeasts. *Yeast.* 10: 1727-1740.

Lai, K. and Elsas, L. J. (2000) Overexpression of human UDP-glucose pyrophosphorylase rescues galactose-1-phosphate uridyltransferase-deficient yeast. *Biochem. Biophys. Res. Commun.* 271: 392-400.

Maleszka, R. and Schneider, H. (1984) Involvement of oxygen and mitochondrial function in the metabolism of D-xylulose by *Saccharomyces cerevisiae*. *Arch. Biochem. Biophy.* 228: 22-30.

Parekh, R. N., Shaw, M. R. and Wittrup, K. D. (1996) An integrating vector for tunable, high copy, stable integration into the dispersed Ty delta sites of *Saccharomyces cerevisiae*. *Biotechnol. Prog.* 12: 16-21.

Reifenberger, E., Boles, E. and Ciriacy, M. (1997) Kinetic characterization of individual hexose transporters of *Saccharomyces cerevisiae* and their relation to the triggering mechanisms of glucose repression. *Eur. J. Biochem.* 245: 324-333.

Richard, P., Toivari, M. H. and Penttila, M. (2000) The role of xylulokinase in *Saccharomyces cerevisiae* xylulose catabolism. *FEMS Microbiol. Lett.* 190: 39-43.

Rizzi, M., Harwart, K., Erlemann, P., Buithanh, N. A. and Dellweg, H. (1989) Purification and properties of the NAD+ xylitol dehydrogenase from the yeast *Pichia stipitis* 0.5. *J Ferment. Bioeng.* 67: 20-24.

Rodriguez-Pena, J. M., Cid, V. J., Arroyo, J. and Nombela, C. (1998) The YGR194c (XKS1) gene encodes the xylulokinase from the budding yeast *Saccharomyces cerevisiae*. *FEMS Microbiol. Lett.* 162:155-160.

Rose, M. D., Winston, F. and Hieter, P. (1990) *Methods in yeast genetics A Laboratory Course Manual.* Cold Spring Harbor, N.Y.: Cold Spring Harbor Laboratory Press.

Senac, T. and Hahn-Hagedahl, B. (1990) Intermediary metabolite concentrations in xylulose- and glucose-fermenting *Saccharomyces cerevisiae* cells. *Appl. Envinron. Microbiol.* 56: 120-126.

Shamanna, D. K. and Sanderson, K. E. (1979) Uptake and catabolism of D-xylose in *Salmonella typhimurium* LT2. *J. Bacteriol.* 139: 64-70.

Sikorski, R. S. and Hieter, P. (1989) A system of shuttle vectors and yeast host strains designed for efficient manipulation of DNA in *Saccharomyces cerevisiae*. *Genetics.* 122: 19-27.

Tantirungkij, M., Nakashima, N., Seki, T. and Yoshida, T. (1993) Construction of xylose-assimilating *Saccharomyces cerevisiae*. *J. Ferment. Bioeng.* 75: 83-88.

Tantirungkij, M., Izuishi, T., Seki, T. and Yoshida, T. (1994) Fed-batch fermentation of xylose by a fast-growing mutant of xylose-assimilating recombinant *Saccharomyces cerevisiae*. *Appl. Microbiol. Biotechnol.* 41: 8-12.

Teusink, B., Walsh, M. C., van Dam, K. and Westerhoff, H. V. (1998) The danger of metabolic pathways with turbo design. *Trends Biochem. Sci.* 23: 162-169.

Thevelein, J. M. and Hohmann, S. (1995) Trehalose synthase: guard to the gate of glycolysis in yeast? *Trends. Biochem. Sci.* 20: 3-10.

Toivari, M. H., Aristidou, A., Ruohonen, L. and Penttila, M. (2001) Conversion of xylose to ethanol by recombinant *Saccharomyces cerevisiae*: importance of xylulokinase (XKS1) and oxygen availability. *Metab. Eng.* 3: 236-249.

Walfridsson, M., Anderlund, M., Bao, X. and Hahn-Hägerdal, B. (1997) Expression of different levels of enzymes from the *Pichia stipitis* XYL1 and XYL2 genes in *Saccharomyces cerevisiae* and its effects on product formation during xylose utilisation. *Appl. Microbiol. Biotechnol.* 48: 218-224.

Wang, P. P. and Schneider, H. (1980) Growth of yeasts on D-xylulose. *Can. J. Microbiol.* 26: 1165-1168.

We claim:

1. A recombinant xylose-fermenting respiration deficient *Saccharomyces cerevisiae* yeast strain comprising heterologous polynucleotide sequences encoding xylose reductase, xylitol dehydrogenase, and D-xylulokinase.

2. The recombinant strain of claim 1, wherein the strain has reduced respiration relative to that of the strain from which it was derived.

3. The recombinant strain of claim 1, wherein the strain is deposited as NRRL Y-30603.

4. A method of producing ethanol from the fermentation of xylose comprising: culturing the recombinant strain of claim 1 with xylose-containing material under suitable conditions for a period of time sufficient to allow fermentation of xylose to ethanol.

5. The method of claim 4, wherein the recombinant strain is caused to have reduced respiration relative to the strain from which it was derived.

6. The method of claim 4, wherein the recombinant strain ferments xylose to ethanol at a higher rate than the strain from which it was derived.

7. The method of claim 5, wherein the recombinant strain is the strain deposited as NRRL Y-30603.

8. The recombinant strain of claim 1, wherein the yeast is a petite mutant.

9. The method of claim 4, wherein the recombinant strain is deposited as NRRL Y-30602.

10. The method of claim 4, wherein the recombinant strain is a respiration deficient mutant of the strain deposited as NRRL Y-30602.

11. A recombinant *Saccharomyces cerevisiae* strain deposited as NRRL Y-30602.

12. A respiration deficient mutant of the recombinant *Saccharomyces cerevisiae* strain of claim 11.

* * * * *

SEQUENCE LISTING

<160> NUMBER OF SEQ ID NOS: 9

<210> SEQ ID NO 1
<211> LENGTH: 23
<212> TYPE: DNA
<213> ORGANISM: Saccharomyces cerevisiae

<400> SEQUENCE: 1
gataccttcg tcaatggcct tct                                    23

<210> SEQ ID NO 2
<211> LENGTH: 17
<212> TYPE: DNA
<213> ORGANISM: Saccharomyces cerevisiae

<400> SEQUENCE: 2
ttcgacggtg ccgaaga                                           17

<210> SEQ ID NO 3
<211> LENGTH: 17
<212> TYPE: DNA
<213> ORGANISM: Saccharomyces cerevisiae

<400> SEQUENCE: 3
ttcgacggtg ccgaaga                                           17

<210> SEQ ID NO 4
<211> LENGTH: 23
<212> TYPE: DNA
<213> ORGANISM: Saccharomyces cerevisiae

<400> SEQUENCE: 4
gataccttcg tcaatggcct tct                                    23

<210> SEQ ID NO 5
<211> LENGTH: 25
<212> TYPE: DNA
<213> ORGANISM: Saccharomyces cerevisiae

<400> SEQUENCE: 5
gaaggtgaca ttgcctctta ctttg                                  25

<210> SEQ ID NO 6
<211> LENGTH: 24
<212> TYPE: DNA
<213> ORGANISM: Saccharomyces cerevisiae

<400> SEQUENCE: 6
tccggtgaac gagtagattt taca                                   24

```
<210> SEQ ID NO 7
<211> LENGTH: 38
<212> TYPE: DNA
<213> ORGANISM: Saccharomyces cerevisiae

<400> SEQUENCE: 7
ggccagtgaa ttgtaatacg actcatatag ggaggcgg                              38

<210> SEQ ID NO 8
<211> LENGTH: 24
<212> TYPE: DNA
<213> ORGANISM: Saccharomyces cerevisiae

<400> SEQUENCE: 8
ctgtaagaag aattgcacgg tccc                                              24

<210> SEQ ID NO 9
<211> LENGTH: 22
<212> TYPE: DNA
<213> ORGANISM: Saccharomyces cerevisiae

<400> SEQUENCE: 9
tcaaaatggc gtgaggtaga ga                                                22
```